(12) United States Patent
Shinkazh

(10) Patent No.: US 10,324,070 B2
(45) Date of Patent: Jun. 18, 2019

(54) HIGH EFFICIENCY CONTINUOUS COUNTERCURRENT TANGENTIAL CHROMATOGRAPHY

(71) Applicant: CHROMATAN INC., State College, PA (US)

(72) Inventor: Oleg Shinkazh, State College, PA (US)

(73) Assignee: CHROMATAN INC., State College, PA (US)

( * ) Notice: Subject to any disclaimer, the term of this patent is extended or adjusted under 35 U.S.C. 154(b) by 119 days.

(21) Appl. No.: 15/305,850

(22) PCT Filed: Apr. 22, 2015

(86) PCT No.: PCT/US2015/027108
§ 371 (c)(1),
(2) Date: Oct. 21, 2016

(87) PCT Pub. No.: WO2015/164511
PCT Pub. Date: Oct. 29, 2015

(65) Prior Publication Data
US 2017/0045483 A1    Feb. 16, 2017

Related U.S. Application Data

(60) Provisional application No. 61/983,186, filed on Apr. 23, 2014.

(51) Int. Cl.
*B01D 15/18* (2006.01)
*G01N 30/42* (2006.01)
(Continued)

(52) U.S. Cl.
CPC ............. *G01N 30/42* (2013.01); *B01D 15/14* (2013.01); *B01D 15/1807* (2013.01);
(Continued)

(58) Field of Classification Search
CPC .... B01D 15/14; B01D 15/18; B01D 15/1807; B01D 15/3804; B01D 15/203; G01N 30/38; G01N 30/42; G01N 30/58
See application file for complete search history.

(56) References Cited

U.S. PATENT DOCUMENTS 4,530,764 A * 7/1985 Thomas ............... B01D 29/073
                                                        210/637
4,780,210 A   10/1988 Hsia
(Continued)

OTHER PUBLICATIONS

Hydranautics, "Flow configuration," Jan. 23, 2001, 8 pages. (Year: 2001).*

(Continued)

*Primary Examiner* — Katherine Zalasky
(74) *Attorney, Agent, or Firm* — McNees Wallace & Nurick LLC

(57) ABSTRACT

A system, module and method for continuous or batch single-pass countercurrent tangential chromatography are disclosed for bind/elute and negative chromatography applications. The system includes binding, washing, elution (for bind/elute), regeneration, and equilibration single-pass modules. The resin slurry flows in a continuous single pass at steady-state through each module, while corresponding buffers flow countercurrent to the slurry facilitating efficient product and impurity extraction. The module and system include retentate pumps for better process robustness and control. A resin tank configured to be reversibly isolated from the single-pass modules facilitates a closed and disposable system. The method includes receiving unpurified product solution and resin slurry, isolating the resin tank, binding product (bind/elute) or impurities (negative) to the resin slurry, washing impurities from the resin slurry, eluting and capturing pure product from the resin slurry (bind/
(Continued)

elute), regenerating the resin slurry following elution, and providing buffer solutions to all of the single-pass steps.

13 Claims, 21 Drawing Sheets

(51) Int. Cl.
    *B01D 15/38*     (2006.01)
    *B01D 15/20*     (2006.01)
    *G01N 30/58*     (2006.01)
    *B01D 15/14*     (2006.01)

(52) U.S. Cl.
    CPC ....... *B01D 15/203* (2013.01); *B01D 15/3804* (2013.01); *G01N 30/58* (2013.01)

(56) References Cited

U.S. PATENT DOCUMENTS

| | | | |
|---|---|---|---|
| 5,256,294 A * | 10/1993 | van Reis | B01D 61/142 210/137 |
| 5,800,713 A * | 9/1998 | Hartmann | A23L 2/74 210/102 |
| 6,214,221 B1 | 4/2001 | Kopf | |
| 6,383,380 B1 | 5/2002 | Kopf | |
| 6,569,340 B2 | 5/2003 | Kopf | |
| 6,596,172 B1 | 7/2003 | Kopf | |
| 6,946,075 B2 | 9/2005 | Kopf | |
| 7,026,468 B2 | 4/2006 | Nochumson et al. | |
| 7,947,175 B2 | 5/2011 | Shinkazh | |
| 7,988,859 B2 | 8/2011 | Shinkazh | |
| 2002/0170859 A1 | 11/2002 | Kopf | |
| 2003/0205526 A1 * | 11/2003 | Vuong | B01D 61/022 210/652 |
| 2006/0027500 A1 | 2/2006 | Schick | |
| 2006/0118472 A1 | 6/2006 | Schick et al. | |
| 2008/0003211 A1 | 1/2008 | Fogh et al. | |
| 2010/0193434 A1 | 8/2010 | Shinkazh | |

OTHER PUBLICATIONS

International Search Report and Written Opinion, PCT/US/15/27108, filed Apr. 22, 2015.

* cited by examiner

HIGH EFFICIENCY CONTINUOUS COUNTERCURRENT TANGENTIAL CHROMATOGRAPHY

REFERENCE TO RELATED APPLICATIONS

This application claims priority from provisional application U.S. Ser. No. 61/983,186, filed on Apr. 23, 2014, and entitled "High Efficiency Continuous Countercurrent Tangential Chromatography," the entirety of which is hereby incorporated by reference herein.

FIELD OF THE INVENTION

The present invention is generally related to chromatography. More specifically, this invention relates to a method, system, and apparatus of tangential chromatography using countercurrent flow to facilitate separation of the desired product and enhance efficiency of the entire chromatography process.

BACKGROUND OF THE INVENTION

There has been a significant and sustained growth in new drug production featuring monoclonal antibodies and other proteins, approximately 15-20% annually. This growth is due to expanding drug pipelines, as well as more efficient cell lines and bioreactor growth optimizations. The annual bio-production costs are currently estimated at $2.6 billion. One of the most significant investments a drug manufacturer has to make is process chromatography (approximately 30% or $850 million annually).

Chromatography is an integral part of drug production; its purpose in the biotechnology industry is to purify the product proteins from contaminating species. The industry has started to recognize that the efficiency of the chromatography steps which are used to purify the product proteins are no longer keeping up with production demands. There are multiple reasons for this.

First, no significant improvements have been made to the column chromatography process in the past 30 years; most of the work in the industry has been focused on new resin development. A notable exception is membrane chromatography which was recently adopted by the industry.

Second, upstream technology has improved tremendously in the same time period—the bioreactors are larger (up to 20,000 liters), and the titers are much higher (up to 15 g/L compared with 1-2 g/L five years ago). As a result of longer fermentation times, there are generally more impurities in the bioreactor effluent solution. All of the above reasons result in a much heavier load for the downstream purification.

Third, column chromatography has inherent physical limitations. Columns larger than 2 meters in diameter do not scale up. The largest columns in the market are 2 meter diameter and 40 cm bed height. They fit 1,250 L of resin. Assuming a binding capacity of 30 g/L of resin (common Protein A resin capacity for monoclonal antibodies), a single cycle can bind 38 kg. A 20,000 L bioreactor with an output of 10 g/L would produce a load of 200 kg. This means that the biggest column in the market would have to run at least 6 full cycles to process a single batch. The operation can take up to 24 hrs and can result in a significant bottleneck for the manufacturing process.

Finally, in the present marketplace, disposability in the manufacturing process is gaining popularity. Disposable process steps save labor, do not require cleaning validation and are easier to run for the manufacturing personnel. Strides have been made in most downstream processes to have disposable systems. These include bioreactors (up to 2,000 L from Xcellerex Corp.), microfiltration (KleenPak TFF technology from Pall Corp.), depth filtration (POD from Millipore Corp.), sterile filtration (all major manufacturers), tangential flow filtration (all major manufacturers) and membrane chromatography (Mustang, Pall Corp., Sartobind, and Sartorius Corp.). In the past three years, disposable pre-packed chromatography columns have been brought to market by Repligen (OPUS) and W.R. Grace (ProVance). These products may provide ease of use and speed in clinical manufacturing, but are generally considered to be too expensive to use in commercial and large scale manufacturing due to the inherent limitations of the column format.

U.S. Pat. Nos. 7,947,175 and 7,988,859 to Oleg Shinkazh, entitled, "Continuous Countercurrent Tangential Chromatography" and "Countercurrent Tangential Chromatography Methods, Systems and Apparatus", respectively, disclose methods, systems and apparatus for a new technique of continuous countercurrent tangential chromatography, which address some of the challenges of the prior art. U.S. Pat. Nos. 7,947,175 and 7,988,859 are incorporated herein in their entirety as if fully restated. However, a method, system, and apparatus of tangential chromatography using countercurrent flow including improvements in pressure profile, economics, productivity, robustness and reduced complexity would be desirable in the art.

BRIEF DESCRIPTION OF THE INVENTION

In an exemplary embodiment, a system for continuous, single-pass countercurrent tangential chromatography having multiple single-pass modules comprises a single-pass binding step module for binding product from an unpurified product solution with a resin slurry, a single-pass washing step module for washing impurities from the resin slurry, a single-pass elution step module for eluting an output of the washing stage module as purified product solution, a single-pass regeneration step module for regenerating the resin slurry, and a resin tank for containing the resin slurry, the resin tank being configured to be reversibly isolated from the multiple single-pass modules following discharge of the resin slurry from the resin tank into the multiple single-pass modules. Each single-pass module includes at least one retentate pump. The resin slurry flows in a continuous single pass at steady-state through each of the single-pass modules, and one or more of the single-pass modules comprises two or more stages with permeate flow directed countercurrent to resin slurry flow within that single-pass module.

In another exemplary embodiment, a module comprises a first input port for receiving an input solution, a first mixer for mixing the input solution with a recycled solution from a second input port to produce a first mixed output, a stage I filter for concentrating the first mixed output to produce stage I retentate, wherein stage I permeate exits the module from the stage I filter via a first output port, a second mixer for mixing the stage I retentate from the stage I filter and an optional buffer solution from a third input port to produce a second mixed output, a stage II filter in series with the stage I filter for concentrating the second mixed output to produce stage II retentate which exits the module from the stage II filter via a second output port, wherein stage II permeate exits the module from the stage II filter via a third output port, and at least one retentate pump. The input solution from input port flows through the stage I filter and the stage II filter in a single pass, and recycled solution from the third output port flows countercurrent to the input solution into the second input port.

In another exemplary embodiment, a method for continuous, single-pass countercurrent tangential chromatography having multiple single-pass steps comprises receiving unpurified product solution from an upstream process, receiving resin slurry from a resin tank for containing the resin slurry, the resin tank being isolated following discharge of the resin slurry from the resin tank, a single-pass binding step for binding product in the unpurified product solution to the resin slurry from the resin tank, a single-pass washing step for washing impurities from the resin slurry, a single-pass elution step for eluting product from the resin slurry after the washing step, capturing purified product solution from the elution step, a single-pass regeneration step for cleaning the resin slurry after the elution step, and providing buffer solutions for the single-pass steps. The resin slurry flows in a continuous single pass at steady-state through each of the single-pass steps, and one or more of the single-pass steps comprises two or more stages with permeate flow directed countercurrent to resin slurry flow within that single-pass stage.

In another exemplary embodiment, a system for continuous, single-pass countercurrent tangential negative chromatography having multiple single-pass modules comprises a single-pass binding step module for binding impurities from an unpurified product solution with a resin slurry, a single-pass washing step module for washing out a purified product solution from the resin slurry, a single-pass regeneration step module for regenerating the resin slurry, and a single-pass equilibration step module for equilibrating the resin slurry. The resin slurry flows in a continuous, single-pass through each of the single-pass modules, and one or more of the single-pass modules comprise two or more stages with permeate flow directed countercurrent to resin slurry flow within that single-pass module.

In another exemplary embodiment, a method for continuous, single-pass countercurrent tangential negative chromatography having multiple single-pass steps, comprises receiving unpurified product solution from an upstream process, receiving resin slurry from a resin source, a single-pass binding step for binding impurities in the unpurified product solution to the resin slurry from the resin source, a single-pass washing step for washing out a purified product solution from the resin slurry, capturing the purified product solution from the binding step and the washing step, a single-pass regeneration step for regenerating the resin slurry, a single-pass equilibration step for equilibrating the resin slurry, and providing buffer solutions for the single-pass steps. The resin slurry flows in a continuous single pass through each of the single-pass steps and one or more of the single-pass steps comprise two or more stages with permeate flow directed countercurrent to resin slurry flow within that single-pass stage.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

FIG. 2A is a schematic representation of flow in a module containing a single stage, according to an embodiment of the present disclosure, while

DETAILED DESCRIPTION OF THE INVENTION

Figure 1:
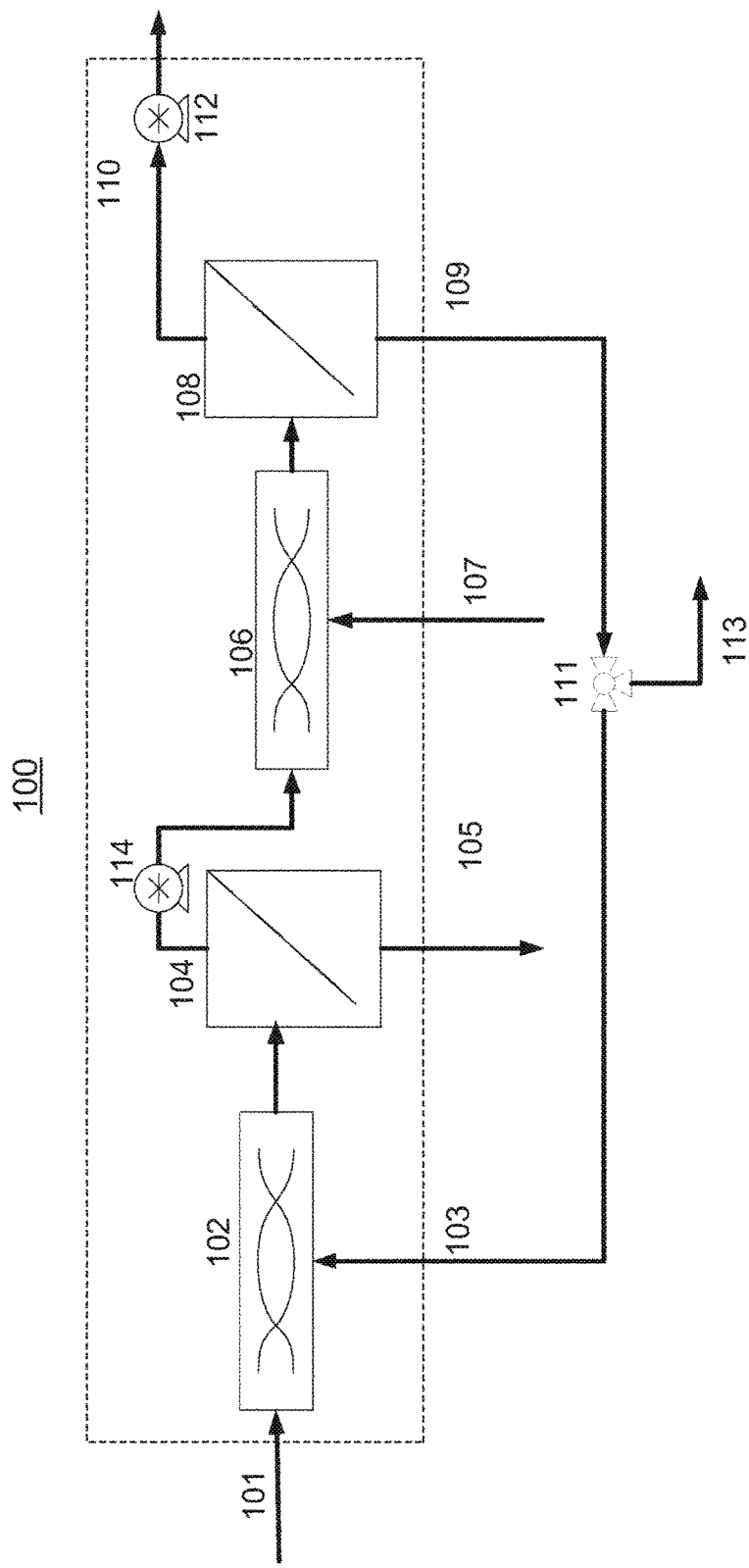
FIG. 1 is a schematic representation of a module for countercurrent tangential chromatography, according to an embodiment of the present disclosure.

Definitions: The following terms of art shall have the below ascribed meanings throughout this Specification.

"Binding" step or mode indicates operation during which resin and unpurified product form a reversible complex (for positive chromatography), or during which resin and impurities form a reversible complex (for negative chromatography).

"Washing" step or mode indicates operation during which resin with bound product is washed with a washing buffer to rid the resin of impurities (for positive chromatography), or during which resin with bound impurities is washed with a washing buffer to wash out carryover product from the binding step (for negative chromatography).

"Elution" step or mode indicates operation during which the complex of resin and the product is reversed and the purified product is collected.

"Regeneration" step or mode indicates operation during which the resin is cleaned for the purpose of reuse or for later cycles.

"Equilibration" step or mode indicates operation during which the system is equilibrated in a neutral buffer.

"Stage" indicates an interconnected tangential flow filter and mixer.

"Single-pass module" is a module that performs one of the chromatographic operations, such as binding, washing, elution, regeneration, and equilibration in a single-pass.

Provided are exemplary systems, modules and methods. Embodiments of the present disclosure, in comparison to systems, modules and methods not utilizing one or more features disclosed herein, provide scalable, reliable and disposable technology that utilizes a principle of recycling to significantly increase process efficiency, increase the scale of operation, and decrease resin costs.

In the present invention, a chromatography column is replaced by a system comprising modules that include one or more stages. Each stage includes a mixer interconnected with a tangential flow filter. The chromatography resin flows through this module in a single pass, while operations corresponding to the operations of a standard chromatographic process are performed on the resin with corresponding buffers (i.e., binding, washing, elution, regeneration, and equilibration). The buffers for operations that utilize more than one stage are pumped into the corresponding modules in a countercurrent direction to the flow of resin, and permeate solutions from later stages are recycled back into previous stages. This creates concentration gradients in the permeate solutions of the tangential flow filters in the countercurrent direction to resin flow, thus saving buffer volume and increasing process efficiency. In embodiments of positive chromatography (also referred to as "bind/elute chromatography" or simply as "chromatography"), the permeate solutions from binding, washing, equilibration and regeneration operations are put to waste. The permeate solution from the elution operation is the purified product stream which is collected in a separate product tank. In embodiments of negative chromatography, the permeate solutions from binding and washing operations are combined and collected as product in a separate product tank, while the permeate solutions from regeneration and equilibration operations are put to waste (elution operations are not performed).

Referring to FIG. 1, one embodiment of a module 100 for countercurrent tangential chromatography is shown (inside the dotted line). Input solution enters at port 101, and the input solution and any input from port 103 are mixed inside static mixer 102. The output from the static mixer 102 enters a tangential flow filter 104 (also described as a "stage I filter"), from which the permeate exits the module at port 105. The retentate from tangential flow filter 104 is pumped by retentate pump 114 and is fed into static mixer 106, which may receive pure buffer at port 107. The output from static mixer 106 is fed into a tangential flow filter 108 (also described as a "stage II filter"). The retentate is pumped out via retentate pump 112. The permeate flows out of the module at port 109. Three-way valve 111 is utilized to direct flow either to waste 113 or to port 103. The retentate from tangential flow filter 108 exits the module at port 110.

Figure 2A:
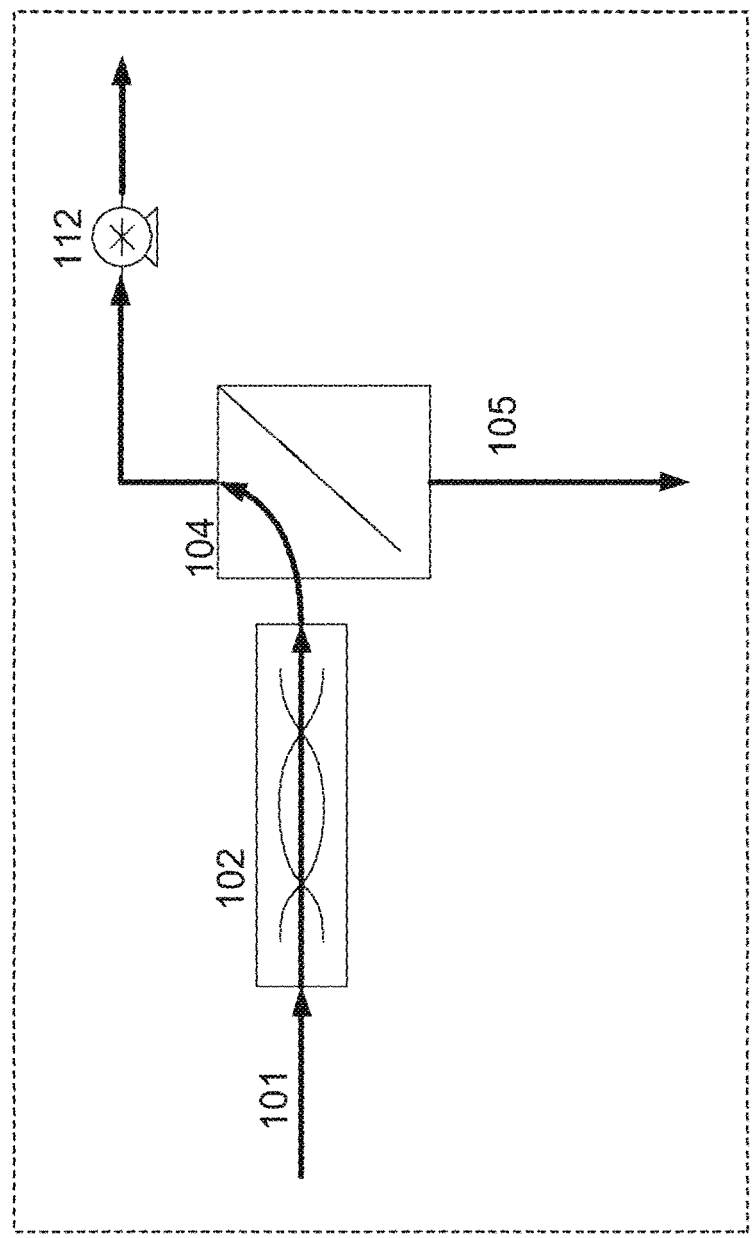

Referring to FIG. 2A, in one embodiment, the mixture of resin and non-purified product solution enters at the left through port 101 (through mixer 102), flows through filter 104 (with permeate exiting as waste at port 105). The retentate is pumped out via retentate pump 112.

Figure 2B:
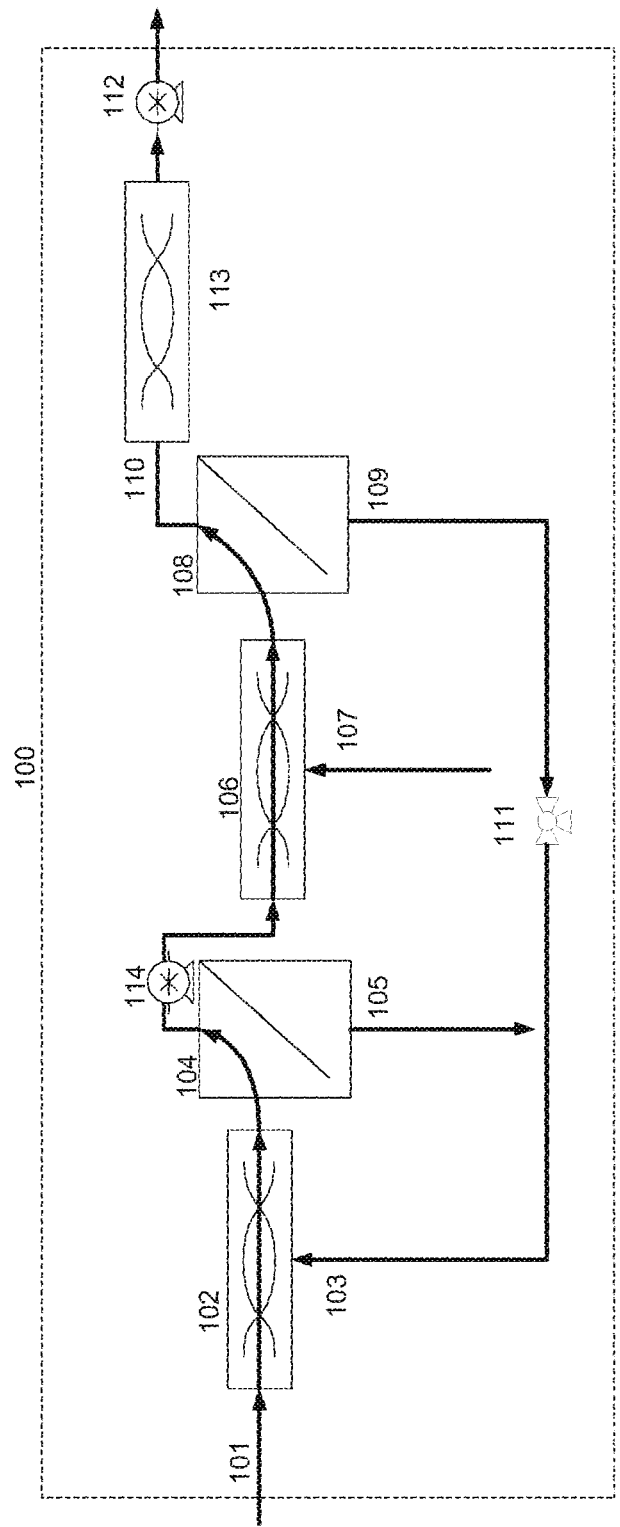
FIG. 2B is a diagrammatic representation of flow in a module containing two stages, according to an embodiment of the present disclosure.

Referring to FIG. 2B, in one embodiment, module 100 includes two stages. The static mixer 113 is called "afterbinder" and is optional. Its purpose is to provide additional residence time in the two-stage binding step in order to increase product binding and yield. Note the single-pass nature of the flow, and the fact that flow is recycled in a countercurrent direction from port 109 to port 103 via three-way valve 111. Note how in this configuration, clean buffer/non-purified product solution enters at port 107, and recycled buffer/non-purified product solution enters at port 103.

Figure 3:
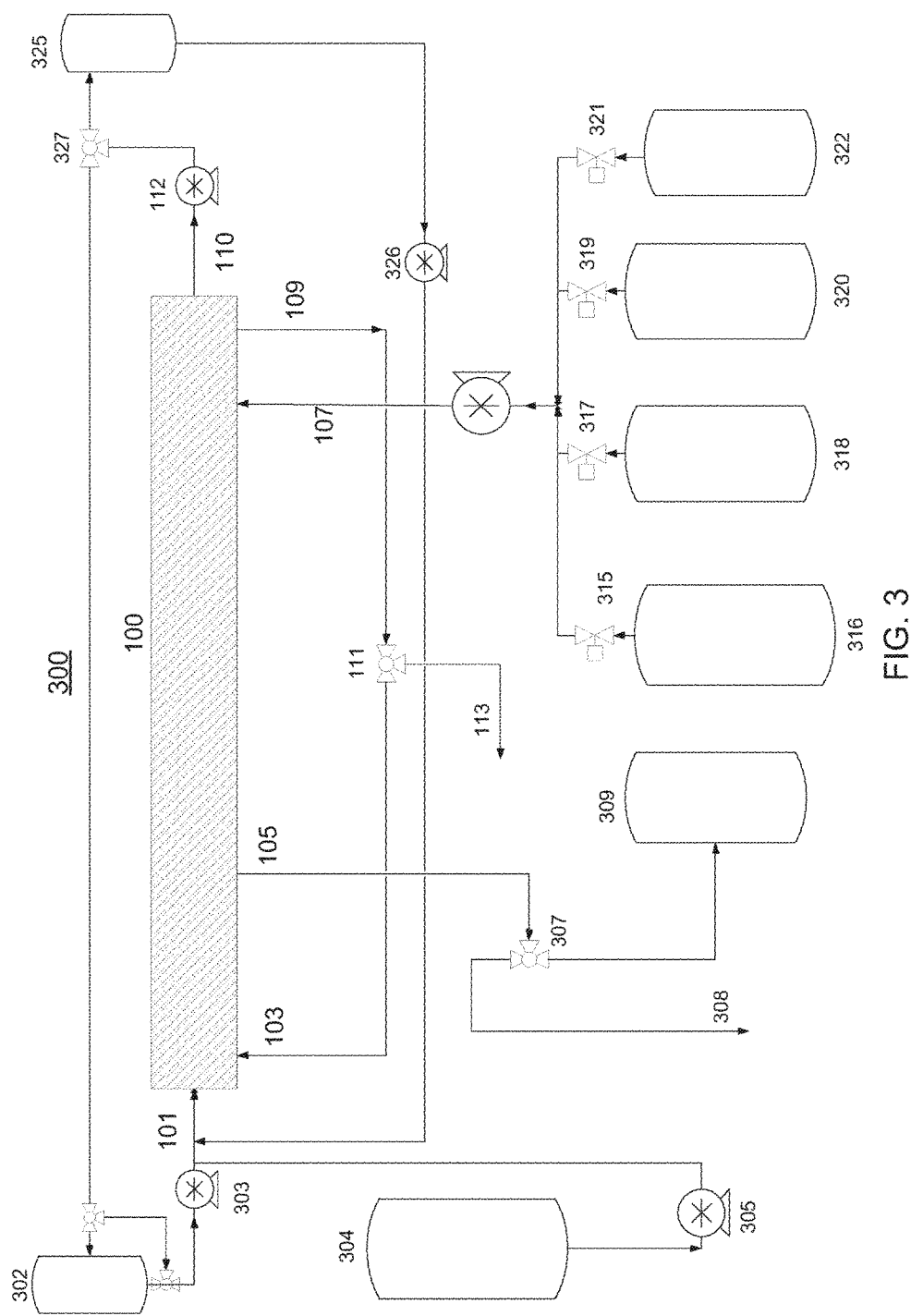
FIG. 3 is a schematic representation of a countercurrent tangential chromatography system operating in batch mode, according to an embodiment of the present disclosure.

Referring to FIG. 3, in one embodiment, a countercurrent tangential chromatography system 300 operating in batch mode is shown. Module 100 operates in the same way as shown and described in relation to FIG. 1. Input port 101 of module 100 is connected to pumps 303, 326, and retentate pump 112. Pump 303 pumps resin from first resin tank 302. Pump 326 pumps resin from second resin tank 325. Pump 305 pumps unpurified product solution from input tank 304. Port 103 of module 100 is connected via three-way valve 111 to port 109 of module 100, as shown in FIG. 1. Waste exits the system at 113. Output from port 105 is connected to a three-way valve 307. Three-way valve 307 is connected to product tank 309 and waste 308. Port 107 receives input into module 100 via pump 314, which is connected to equilibration tank 316, washing tank 318, elution tank 320 and regeneration tank 322 via valves 315, 317, 319 and 321, respectively. Output from port 110 is pumped out via retentate pump 112 and three-way valve 327 to the first resin tank 302 and a second resin tank 325.

The embodiment of the system shown in FIG. 3 is designed to treat the resin using a batch-mode operation. The resin is sequentially treated by different chromatographic processes (binding, washing, elution, regeneration, and equilibration) as it cycles from the first resin tank 302 to the second resin tank 325 and vice versa. For example, during the first stage (binding), resin passes from tank 302 to tank 325 from left to right through module 100 via pump 303. During the next stage (washing) resin passes from tank 325 to tank 302 from left to right through module 100 via pump 326. The other stages (elution, regeneration, and equilibration) alternate tanks in a similar manner. The countercurrent operation during washing, elution, regeneration, and equilibration allows greater efficiency and buffer conservation.

Figure 4:
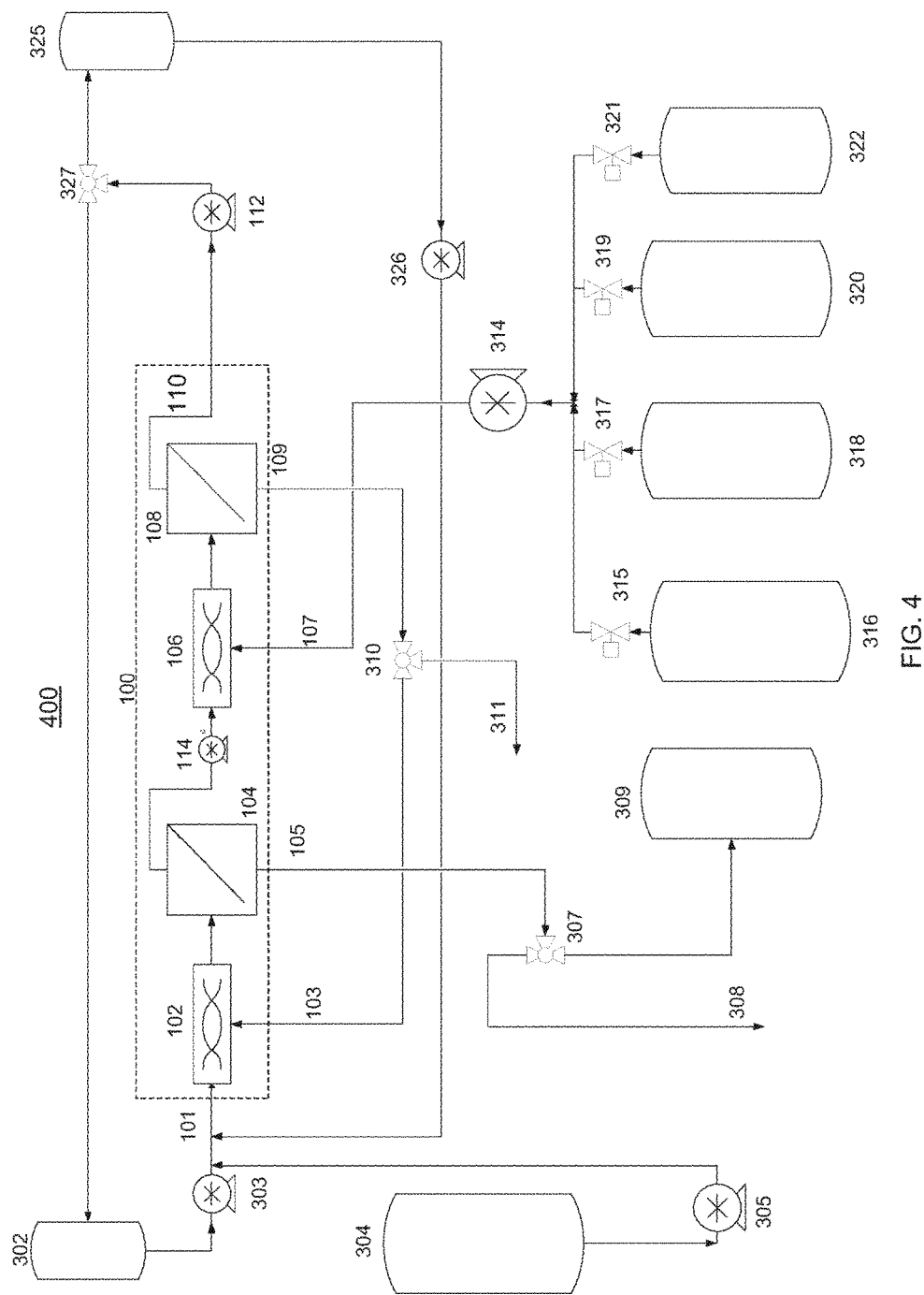
FIG. 4 is a schematic representation of the countercurrent tangential chromatography system of FIG. 3, according to an embodiment of the present disclosure.

Referring to FIG. 4, in one embodiment, a countercurrent tangential chromatography system 400 includes the countercurrent tangential chromatography system 300 (as previously shown in FIG. 3) and module 100 (as previously shown in FIG. 1).

Figure 5:
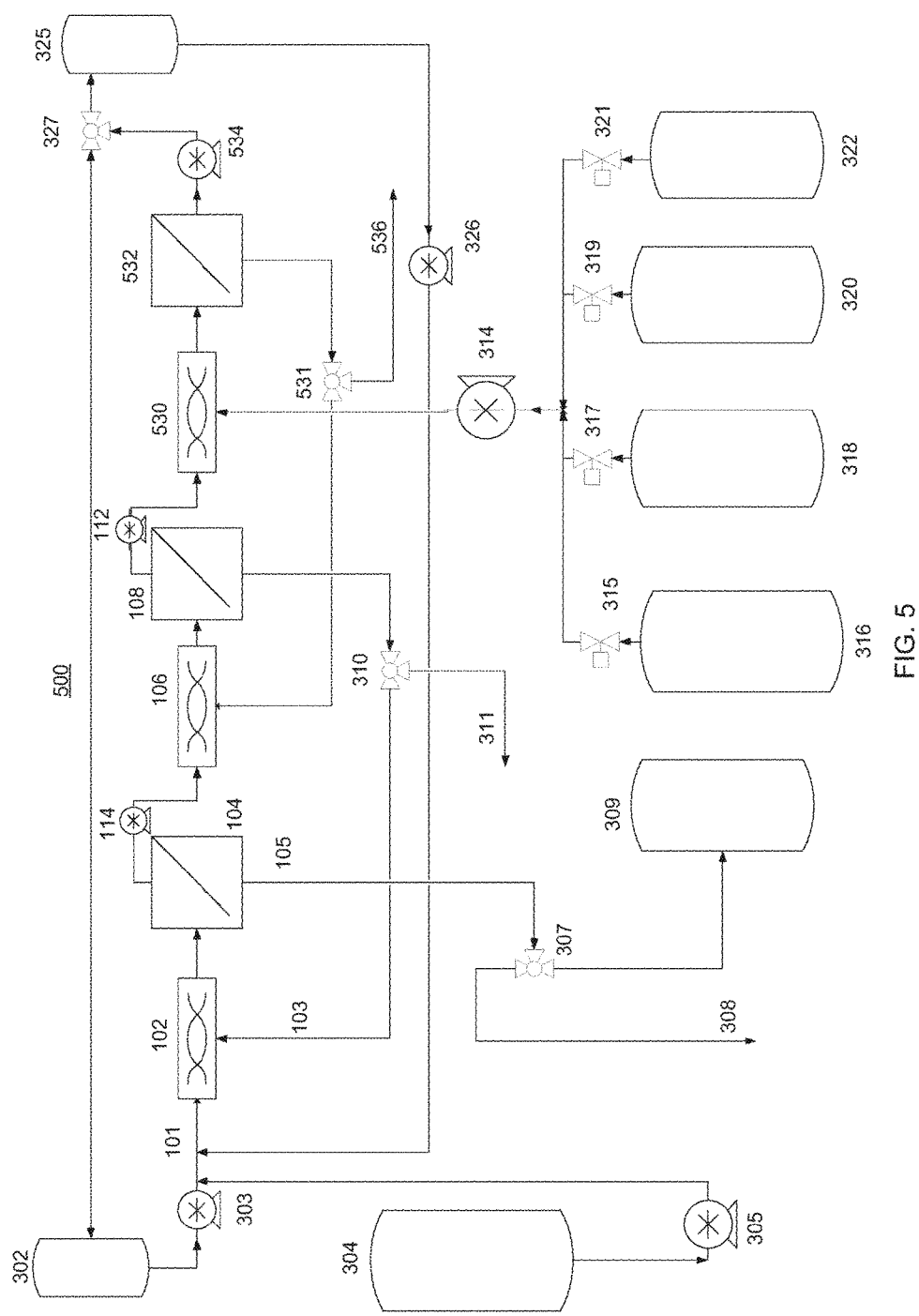
FIG. 5 is a schematic representation of a countercurrent tangential chromatography system, according to an embodiment of the present disclosure.

Referring to FIG. 5, in another embodiment, a countercurrent tangential chromatography system 500 is shown. This embodiment differs from embodiments depicted in FIGS. 3 and 4, by the addition of an additional (third) stage of countercurrent separation, including mixer 530, filter 532, retentate pump 534, and three-way valve 531. Waste exits at 536. Addition of the third stage may increase process efficiency and decrease buffer utilization. It is possible to add more stages (e.g., 4 stages, 5 stages, 6 stages, or more) to any module. However, mathematical modeling, described below, indicates that the addition of more than three stages may result in significantly diminishing returns in terms of process efficiency and buffer utilization.

Figure 6:
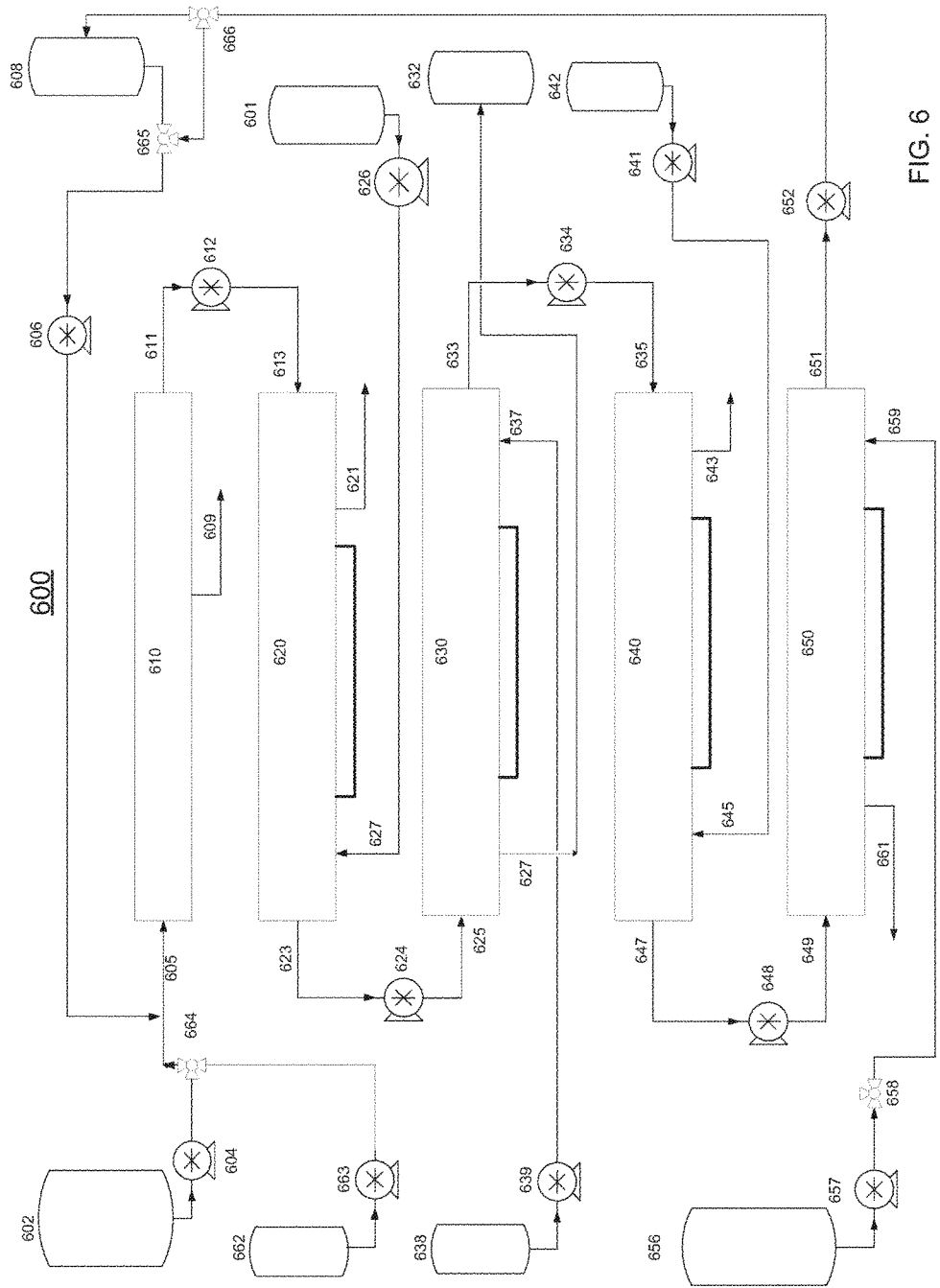
FIG. 6 is a schematic representation of a countercurrent tangential chromatography system operating in continuous mode, according to an embodiment of the present disclosure.

Referring to FIG. 6, in one embodiment, countercurrent tangential chromatography system 600 operates in continuous mode. Modules 610 ("binding stage"), 620 ("washing stage"), 630 ("elution stage"), 640 ("regeneration stage") and 650 ("equilibration stage") operate in an analogous manner to the operation of module 100 shown in FIGS. 1, 2A and 2B. The thick black line on modules 620, 630, 640 and 650 represent a connection of a third output port (as shown as 109 in FIGS. 1 and 2B) and a second input port (as shown as 103 in FIGS. 1 and 2B) via three-way valve (as shown as 111 in FIGS. 1 and 2B). These ports and three-way valves are not shown in FIG. 6 for clarity, but they are present in each of modules 620, 630, 640 and 650.

Binding stage module 610 is connected at port 605 via pump 604 to non-purified product tank 602, via pump 606 to resin tank 608, and via three-way valve 664 and pump 663 to binding buffer tank 662. Port 609 on module 610 goes to waste.

Washing stage module 620 is connected at port 613 via retentate pump 612 to an output port 611 of the binding stage module 610. Port 621 goes to waste. Washing buffer enters at port 627 via pump 626 from washing buffer tank 601.

Elution stage module 630 is connected at port 625 via retentate pump 624 to output port 623 of washing stage module 620. Elution buffer enters at port 637 via pump 639 from elution buffer tank 638. Purified product exits module 630 at port 627 into product storage tank 632.

Regeneration module 640 is connected at port 635 via retentate pump 634 to output port 633 of module 630. Waste exits at port 643. Regeneration buffer enters at port 645 via pump 641 from regeneration buffer tank 642.

Equilibration module 650 is connected at port 649 via retentate pump 648 to output port 647 of regeneration module 640. Resin is pumped out of port 651 via retentate pump 652 into the resin storage tank 608. When the system reaches steady-state, the resin storage tank is bypassed via three way valves 665 and 666. Waste exits from module 650 at port 661. Equilibration buffer enters at port 659 via the three-way valve 658 and the pump 657 from the equilibration buffer tank 656.

Accordingly, unlike the system of FIG. 3, which is designed to treat the resin/product in alternating batch-mode, with resin alternating between the first and the second resin tanks, the system of FIG. 6 is designed to treat the resin/product in a continuous single pass at steady-state, with resin flowing continuously from the resin tank 608, through modules 610, 620, 630, 640, and 650, and returning to resin tank 608. In an alternate embodiment, the resin may be circulated from module 650 back to module 610, bypassing the resin tank, when the system has reached steady-state. Without being bound by theory, it is believed that the continuous nature of the system 600 shown in FIG. 6 allows a fixed amount of resin to be used for processing an essentially unlimited amount of unpurified product, subject only to the lifetime of the resin and process time limitations.

Figure 7A:
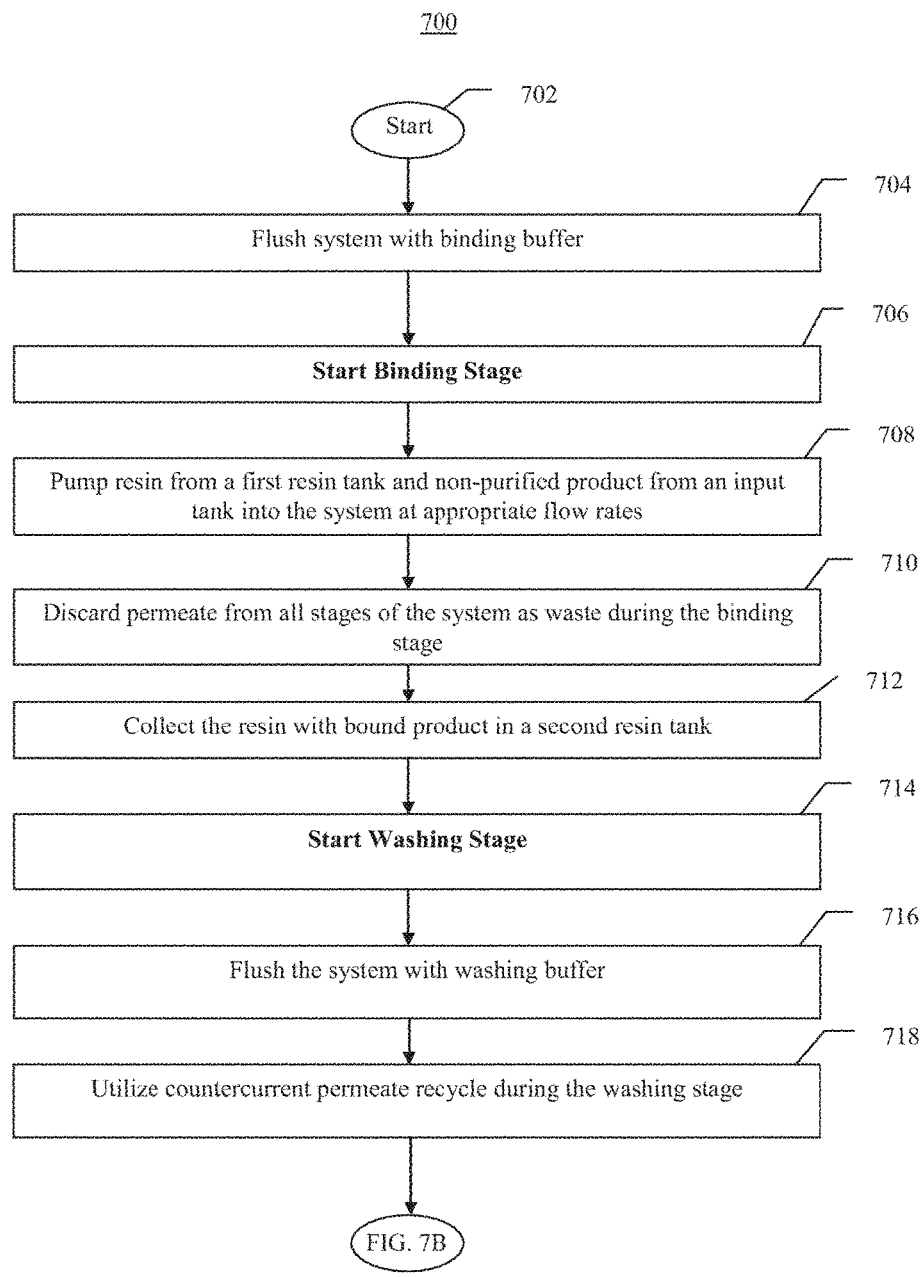
FIGS. 7A, 7B, and 7C detail a process of countercurrent tangential chromatography operating in batch mode, according to an embodiment of the present disclosure.
Figure 7B:
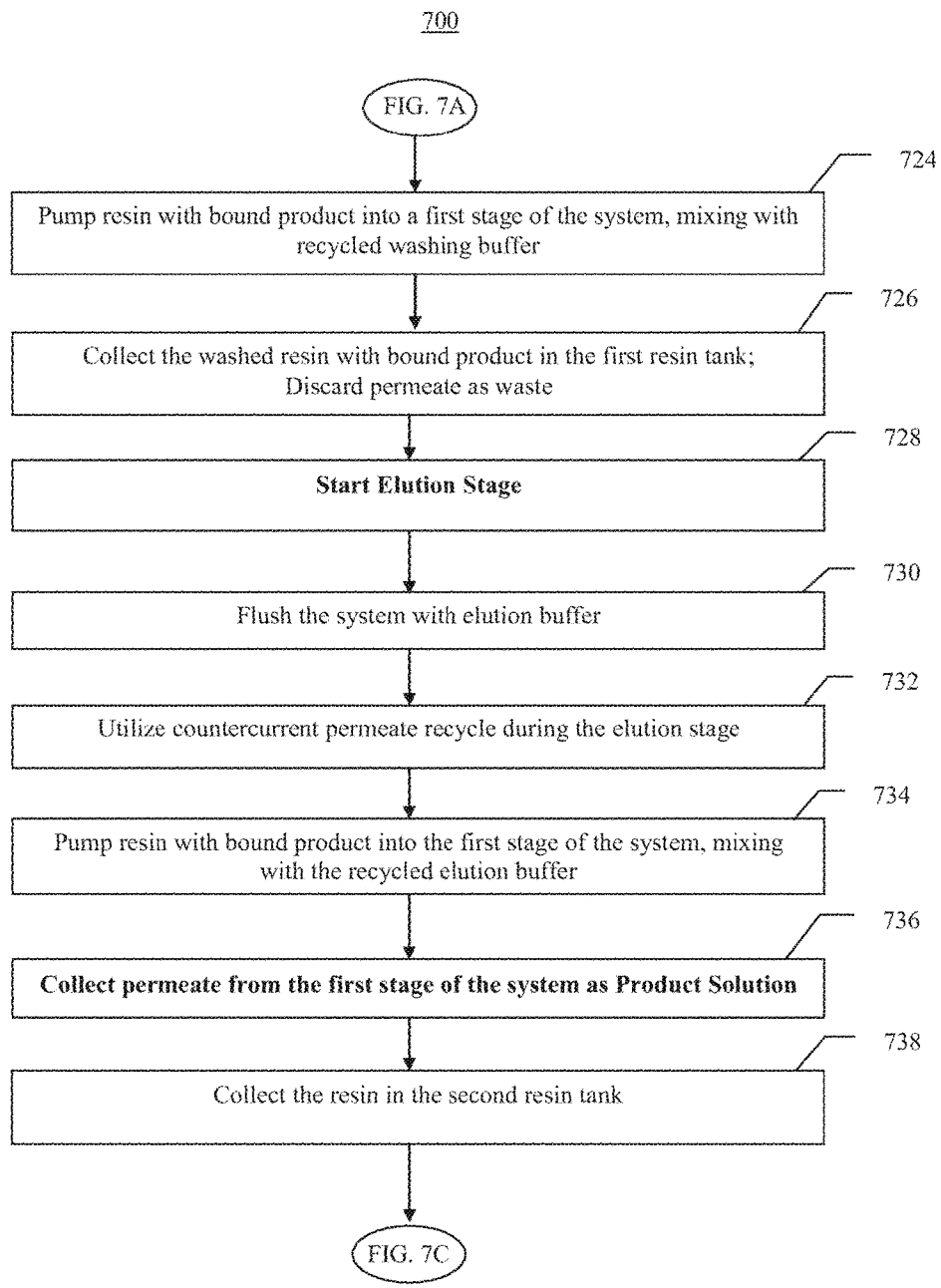
Figure 7C:
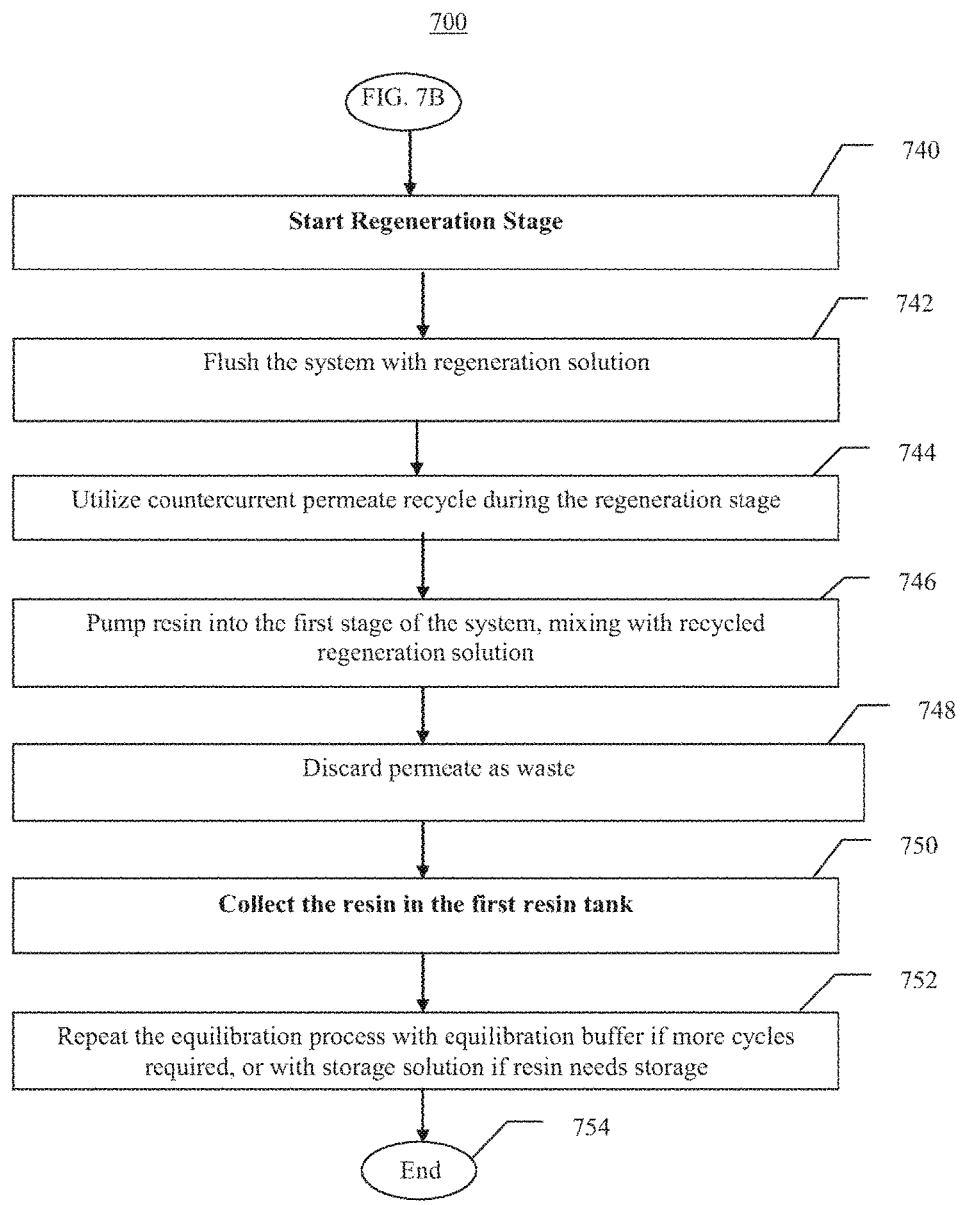

Referring to FIGS. 7A, 7B, and 7C process 700 of countercurrent tangential chromatography operating in batch mode is shown, according to an embodiment of the present invention. Process 700 begins at step 702. The system is flushed with binding buffer, as shown in step 704. In step 706, the binding stage is started (emphasis in bold). Resin and non-purified product is pumped into the system at appropriate flow rates, as shown in step 708. The permeate solutions are discarded from all stages as waste during the binding stage only, as shown in step 710. The resin is collected with bound product as shown in step 712.

In step 714, the washing stage is started (emphasis in bold). The system is flushed with washing buffer, as shown in step 716. The countercurrent permeate is recycled and utilized during the washing stage to improve process efficiency and conserve buffer solution according to the principles of the present invention, as shown in step 718. Resin is pumped with bound product back into the first stage of the system, where it mixes with the recycled wash buffer, as shown in step 724. The washed resin with bound product is collected in the first resin tank, while permeate solution is discarded as waste, as shown in step 726.

In step 728, the elution stage is started (emphasis in bold). The system is flushed with elution buffer, as shown in step 730. The countercurrent permeate is recycled and reused during the elution stage in order to improve process efficiency and to conserve buffer solution, as shown in step 732. Resin bound with product is pumped back into the first stage of the system, where it mixes with the recycled elution solution, as shown in step 734.

In step 736, permeate solution from the first stage is collected as product solution (emphasis in bold). Resin is collected in the second resin tank, as shown in step 738.

In step 740, the regeneration stage is started (emphasis in bold). The system is flushed with regeneration solution, as shown in step 742. The countercurrent permeate is recycled and reused during the regeneration stage, in order to improve process efficiency and to conserve buffer solution, as shown in step 744. The resin is pumped into the first stage, where it mixes with the recycled regeneration solution, as shown in step 746. The permeate solution is discarded as waste, as shown in step 748.

In step 750, the resin is collected in the first resin tank (emphasis in bold), hence completing the cycle and allowing the reuse of resin.

Finally, the equilibration process using equilibration buffer may be repeated if more cycles are required, as shown in step 752. Alternatively, equilibration process may be performed with storage solution if the resin requires storage, as shown in step 752. The process 700 ends in step 754.

Figure 8A:
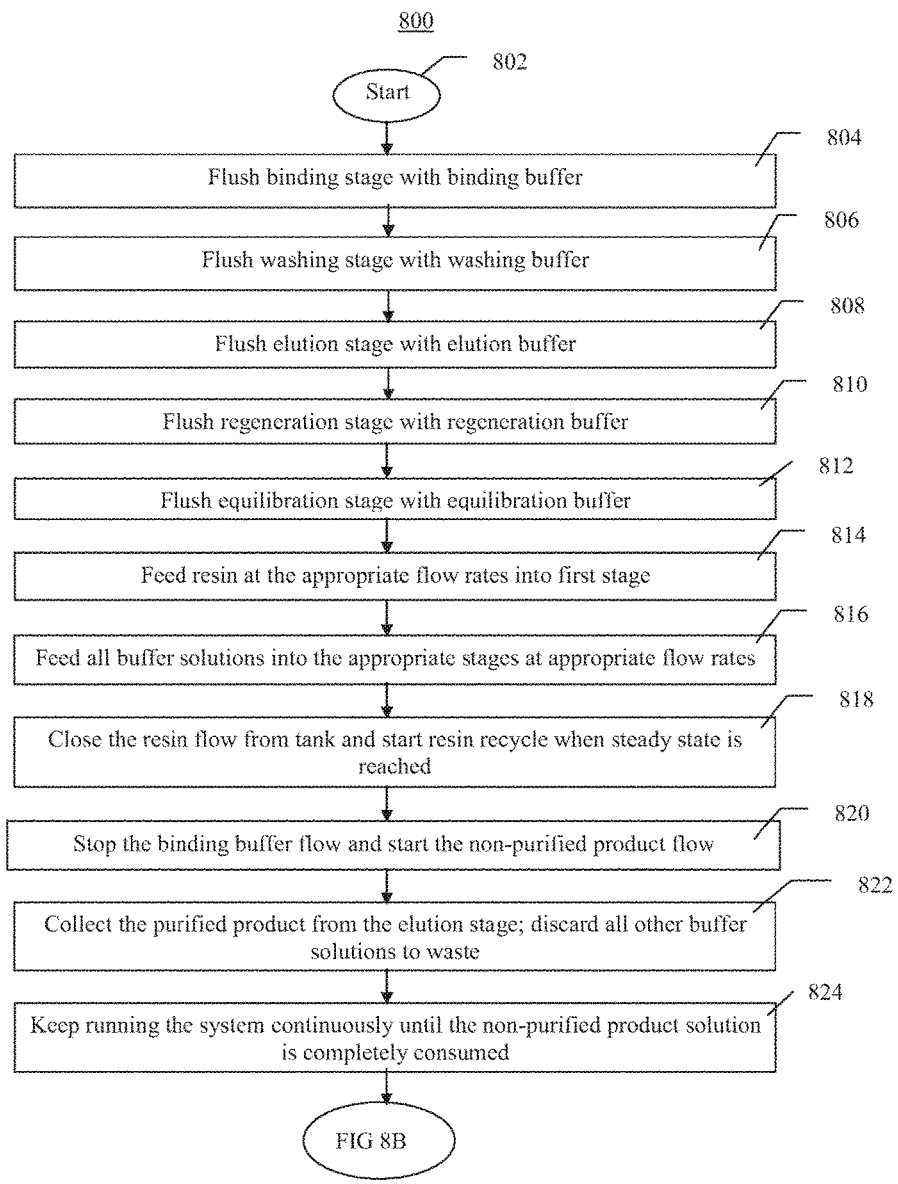
FIGS. 8A and 8B detail a process of countercurrent tangential chromatography operating in continuous mode, according to an embodiment of the present disclosure.
Figure 8B:
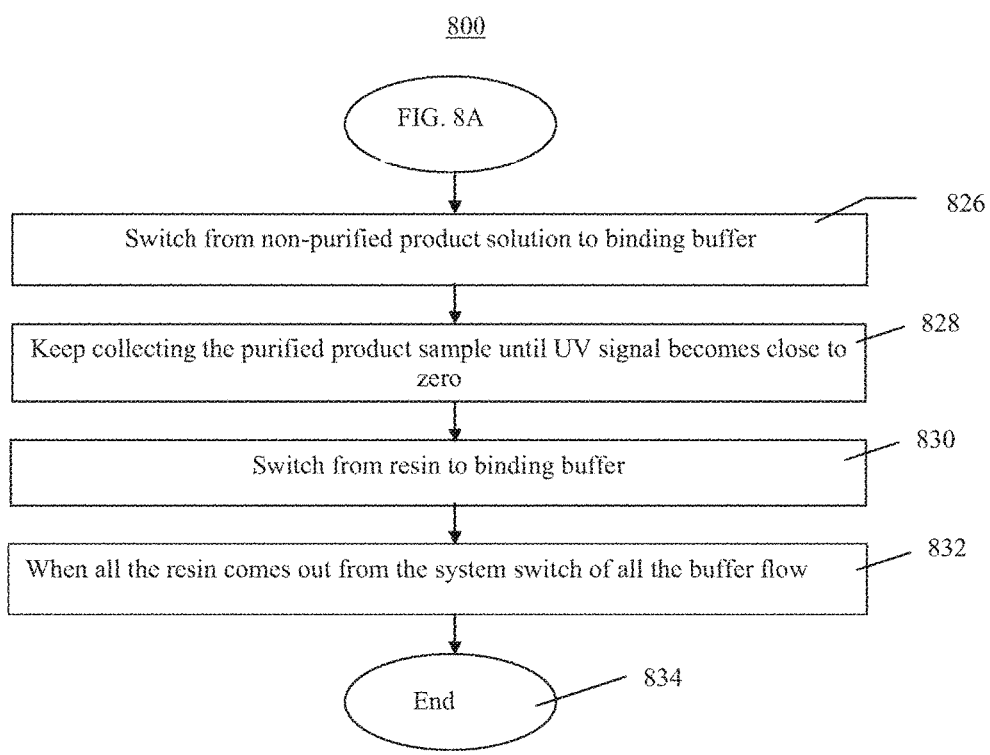

Referring to FIGS. 8A and 8B, a process 800 of countercurrent tangential chromatography operating in continuous mode is shown, according to another embodiment of the present invention. Process 800 begins in step 802. The binding stage (Module 610 of FIG. 6) is flushed with binding buffer, as shown in step 804. The washing stage (Module 620 of FIG. 6) is flushed with washing buffer, as shown in step 806. The elution stage (Module 630 of FIG. 6) is flushed with elution buffer, as shown in step 808. The regeneration stage (Module 640 of FIG. 6) is flushed with regeneration buffer, as shown in step 810. The equilibration stage (Module 650 of FIG. 6) is flushed with equilibration buffer, as shown in step 812. Resin is fed at the appropriate flow rates into the first stage of the system (Module 610 of FIG. 6), as shown in step 814. All buffer solutions are fed into the appropriate stages at appropriate flow rates, as shown in step 816. When the resin concentration reaches steady-state, it is redirected and recycled back to the entrance of the system via the three way valve 665 and 666, as shown in step 818. Binding buffer flow is then interchanged with the unpurified product solution, as shown in step 820. The purified product is collected from the elution stage (Module 630 of FIG. 6), while all other buffer solutions are discarded to waste, as shown in step 822. The entire system is kept running continuously until the non-purified product solution is completely consumed, as shown in step 824. The non-purified product solution is then switched to binding buffer, as shown in step 826. The purified product solution is collected in the product tank until UVA280 signal is close to zero, as shown in step 828. At that point the resin is switched off and the binding buffer is switched on as shown in step 830. After all the resin is recovered from the system, all buffers are shut down, as shown in step 832. The process ends and concludes in disassembly of the apparatus (834).

In one embodiment, the resin is injected into every stage at the same flow rate via retentate pumps (such as, for example, 112 114, 534, 612, 624, 634, 648 and 652), which are installed before every static mixer. In U.S. Pat. Nos. 7,947,175 and 7,988,859, the systems described therein use permeate pumps to recycle buffers. As shown in FIG. 2, the permeate pumps have been removed and the permeate flow is simply equal to buffer flow rate. The hydrodynamics are stabilized by using the steady-state flow of the retentate pumps that serve both as pumps and as quasi check valves that guide the flow of buffer countercurrently to resin through each step. Since each step is acting as a closed system, the buffer pumped into each step will be the same as the resulting flow rate of the permeate stream out of that step.

Figure 9:
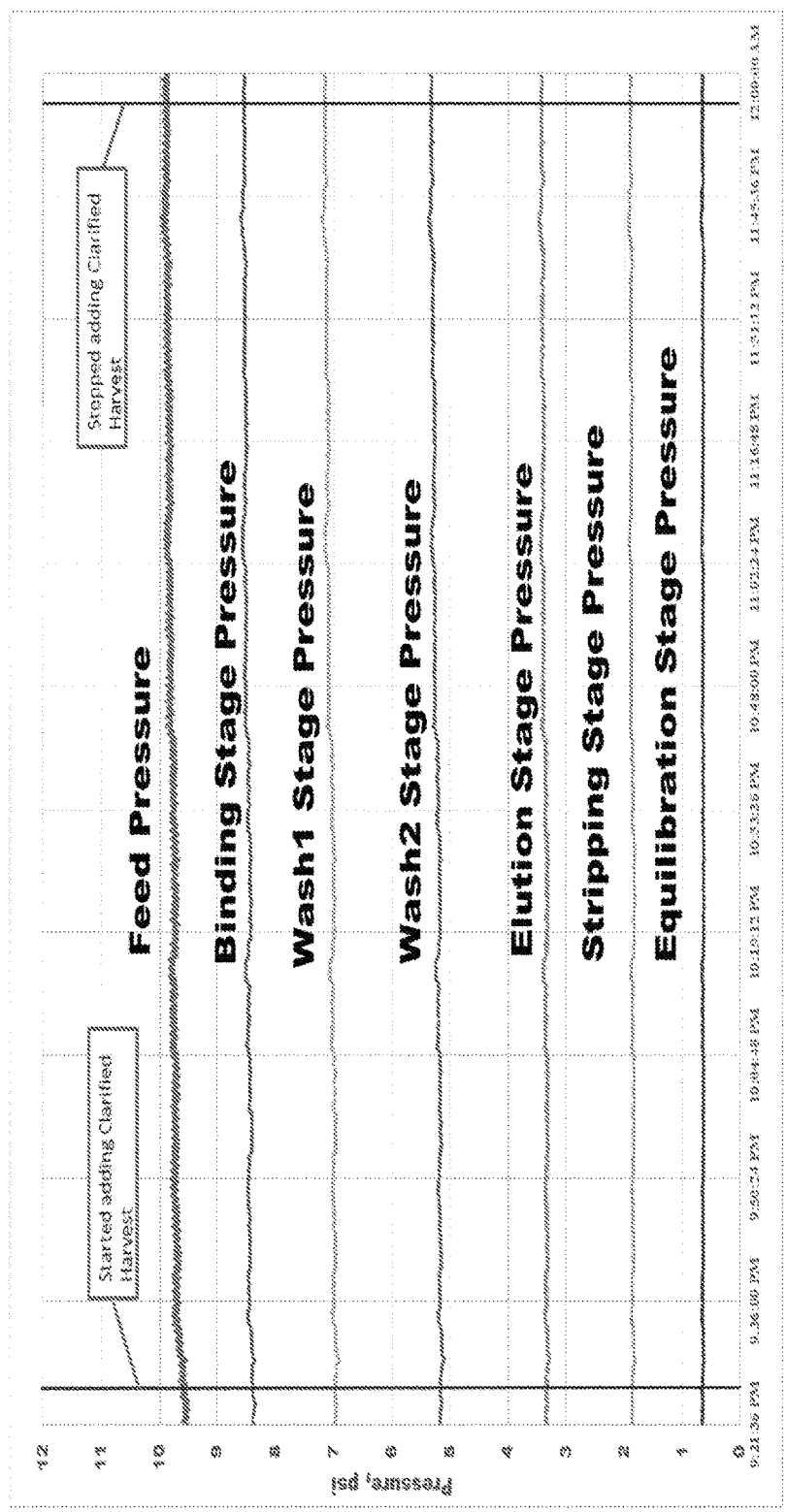
FIG. 9 discloses the pressure profile results of a system lacking some of the features of the present disclosure, showing a net pressure gradient from the binding to equilibration steps.
Figure 10:
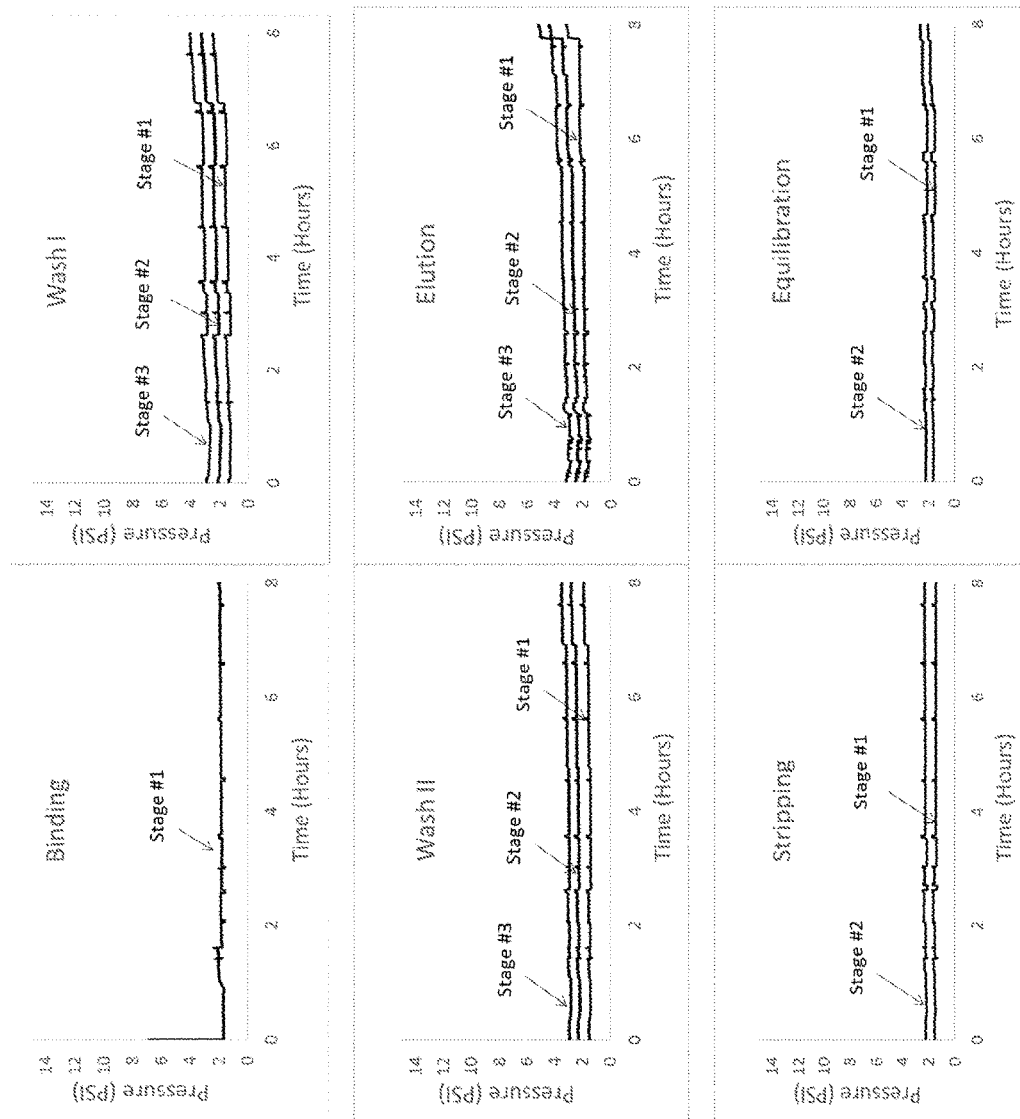
FIG. 10 discloses the pressure profiles of a system, according to an embodiment of the present disclosure, showing very similar pressure profiles for each operational step.

Removing the permeate pumps and introducing retentate pumps such that the system is no longer pressurized by the resin slurry pump, but is instead driven by individual retentate pumps from each step improves the pressure profiles across the entire system. Referring to FIG. 9, in a system including permeate pumps and pressurized by the resin slurry pump, according to U.S. Pat. Nos. 7,947,175 and 7,988,859, each stage operates at a significantly different pressure. In contrast, referring to FIG. 10, and according to an embodiment of the present invention having retentate pumps, operating at steady-state, and including a resin tank for containing the resin slurry, the resin tank being configured to be reversibly isolated from the modules following discharge of the resin slurry from the resin tank into the modules, the pressure profiles for each step are very similar, and the overall pressure of the system decreases by nearly 70%. Significantly more robust flow conditions reduce or eliminate the need for slurry level control, which makes the configuration allowing reversible isolation (bypass) of the resin tank after the resin is ejected from the resin tank practical. In one embodiment, bypassing the resin tank at steady-state conditions decreases the overall amount of the resin and increases the overall productivity (g purified/L of resin/hr) of the system by about 30%. Isolating the resin tank may also increase aseptic control. Additionally, eliminating control of the permeate pump flow rate may eliminate the need for digital scales, decreasing the equipment foot print and increasing system robustness.

In one embodiment, some or all of the components of the system are disposable.

The systems and methods disclosed herein may separate and/or purify any suitable species or substances, including, but not limited to, biologics, enzymes, proteins, peptides, small molecules, amino acids, antibiotics, enantiomers, DNA, plasmids, RNA, siRNA, vaccines, polysaccharides, viruses, prions, virus-like particles, plasma proteins, cells, stem cells, and combinations thereof. The systems and methods disclosed herein may be suitable for or adapted to chiral separations, gas separations, or combinations thereof.

In one embodiment, the systems and methods disclosed herein may be applied to or incorporated in any suitable chromatographic mode, including, but not limited to, negative/flow-through chromatography, affinity chromatography, ion exchange chromatography, hydrophobic interaction chromatography, metal affinity chromatography, mixed mode chromatography, chiral chromatography, reversed phase chromatography, his-tag chromatography, size-exclusion chromatography, or combinations thereof.

Figure 11:
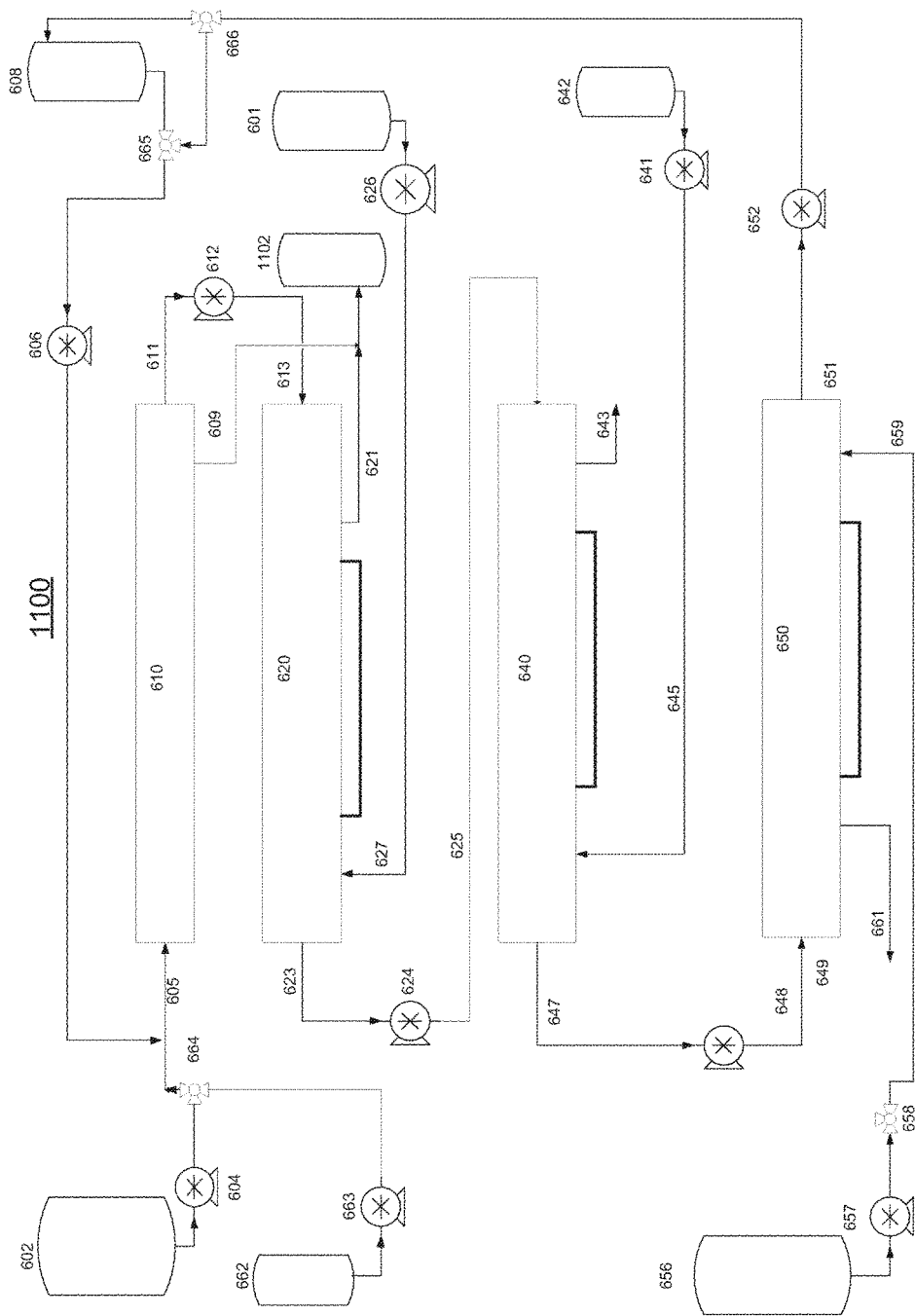
FIG. 11 is a schematic representation of a countercurrent tangential negative chromatography system operating in continuous mode, according to an embodiment of the present disclosure.

Referring to FIG. 11, in one embodiment a countercurrent tangential chromatography system operating in continuous mode is configured for negative chromatography. During negative chromatography, the chromatography resin binds contaminants while not binding the product. Product is recovered in the permeate from the binding and washing steps, while the contaminants are striped and washed to waste in the regeneration and equilibrium steps. Negative chromatography is well suited for trace contaminant removal.

Modules 610 ("binding stage"), 620 ("washing stage"), 640 ("regeneration stage") and 650 ("equilibration stage") operate in an analogous manner to the operation of module 100 shown in FIGS. 1, 2A and 2B. The thick black line on modules 620, 640 and 650 represent a connection of a third output port (as shown as 109 in FIGS. 1 and 2B) and a second input port (as shown as 103 in FIGS. 1 and 2B) via three-way valve (as shown as 111 in FIGS. 1 and 2B). These ports and three-way valves are not shown in FIG. 11 for clarity, but they are present in each of modules 620, 640 and 650.

The contaminants are bound to the slurry in the binding step (610), while product is collected via binding step effluent (609). Additional product is also collected via washing step (620) effluent stream (621). Binding effluent stream (609) and wash effluent stream (621) are then combined and collected in product tank (1102). Module 640 (regeneration step) is used to regenerate the resin and module 650 (equilibration step) is used to equilibrate the slurry to be recycled back to the binding step via pump 652.

Figure 12A:
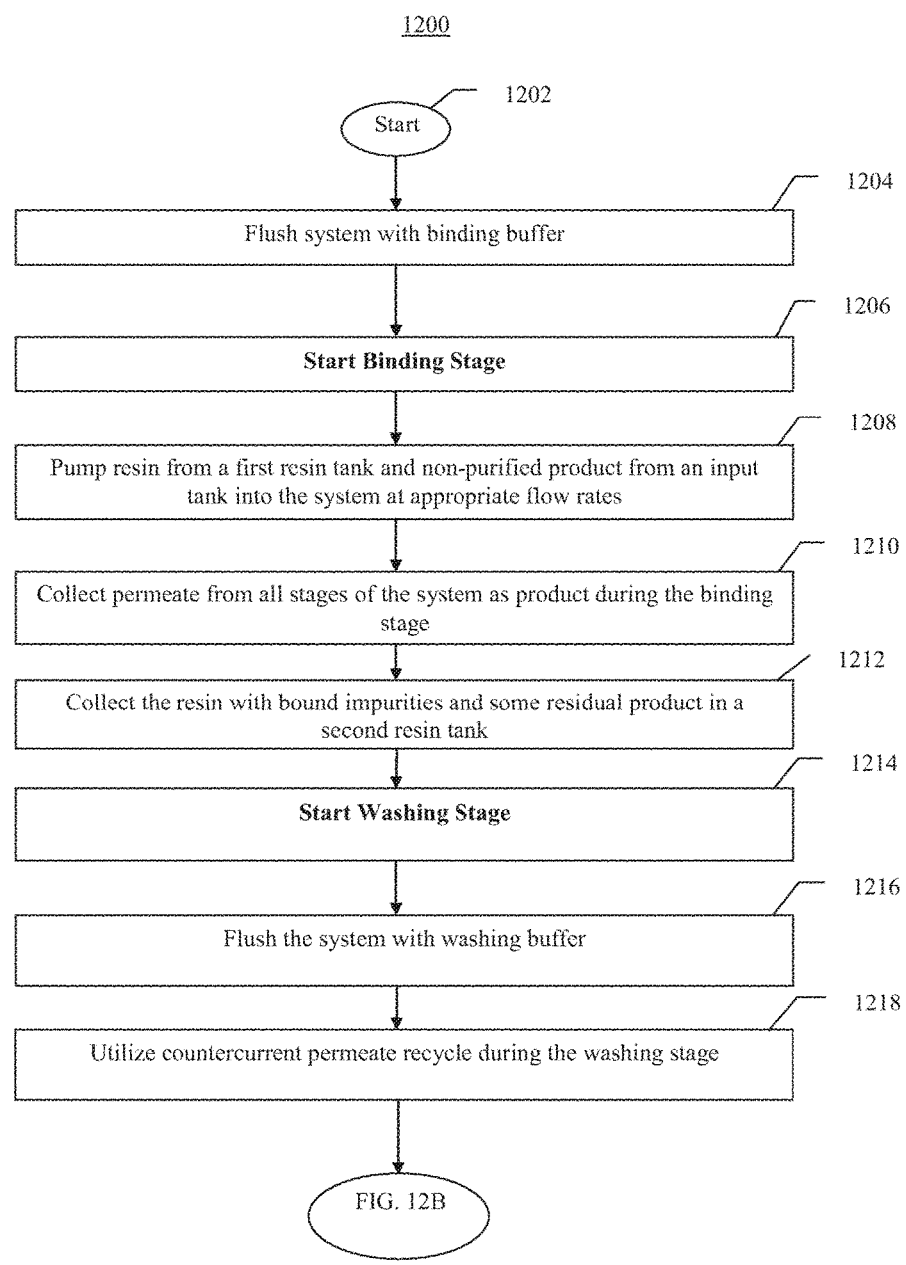
FIGS. 12A and 12B detail a process of countercurrent tangential negative chromatography operating in batch mode, according to an embodiment of the present disclosure.
Figure 12B:
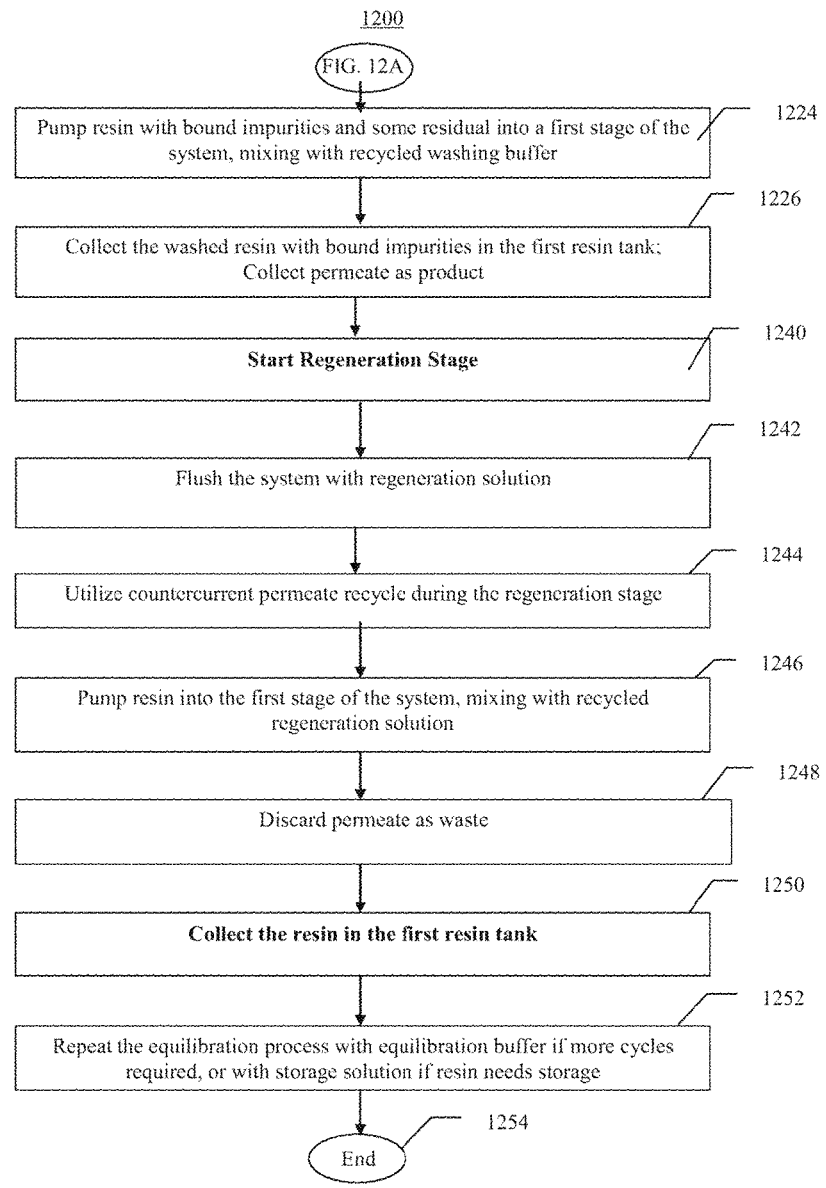

Referring to FIGS. 12A and 12B, process 1200 of countercurrent tangential negative chromatography operating in batch mode is shown, according to an embodiment of the present invention. Process 1200 begins at step 1202. The system is flushed with binding buffer, as shown in step 1204. In step 1206, the binding stage is started (emphasis in bold). Resin and non-purified product is pumped into the system at appropriate flow rates, as shown in step 1208. The permeate solutions are collected from all stages as product, as shown in step 1210. The resin is collected with bound impurities as shown in step 1212.

In step 1214, the washing stage is started (emphasis in bold). The system is flushed with washing buffer, as shown in step 1216. The countercurrent permeate is recycled and utilized during the washing stage to improve process efficiency and conserve buffer solution according to the principles of the present invention, as shown in step 1218. Resin is pumped with bound impurities back into the first stage of the system, where it mixes with the recycled wash buffer, as shown in step 1224. The washed resin with bound impurities is collected in the first resin tank, while permeate solution is collected as product, as shown in step 1226.

In step 1240, the regeneration stage is started (emphasis in bold). The system is flushed with regeneration solution, as shown in step 1242. The countercurrent permeate is recycled and reused during the regeneration stage, in order to improve process efficiency and to conserve buffer solution, as shown in step 1244. The resin is pumped into the first stage, where it mixes with the recycled regeneration solution, as shown in step 1246. The permeate solution is discarded as waste, as shown in step 1248.

In step 1250, the resin is collected in the first resin tank (emphasis in bold), hence completing the cycle and allowing the reuse of resin.

Finally, the equilibration process using equilibration buffer may be repeated if more cycles are required, as shown in step 1252. Alternatively, equilibration process may be performed with storage solution if the resin requires storage, as shown in step 1252. The process 1200 ends in step 1254.

Figure 13A:
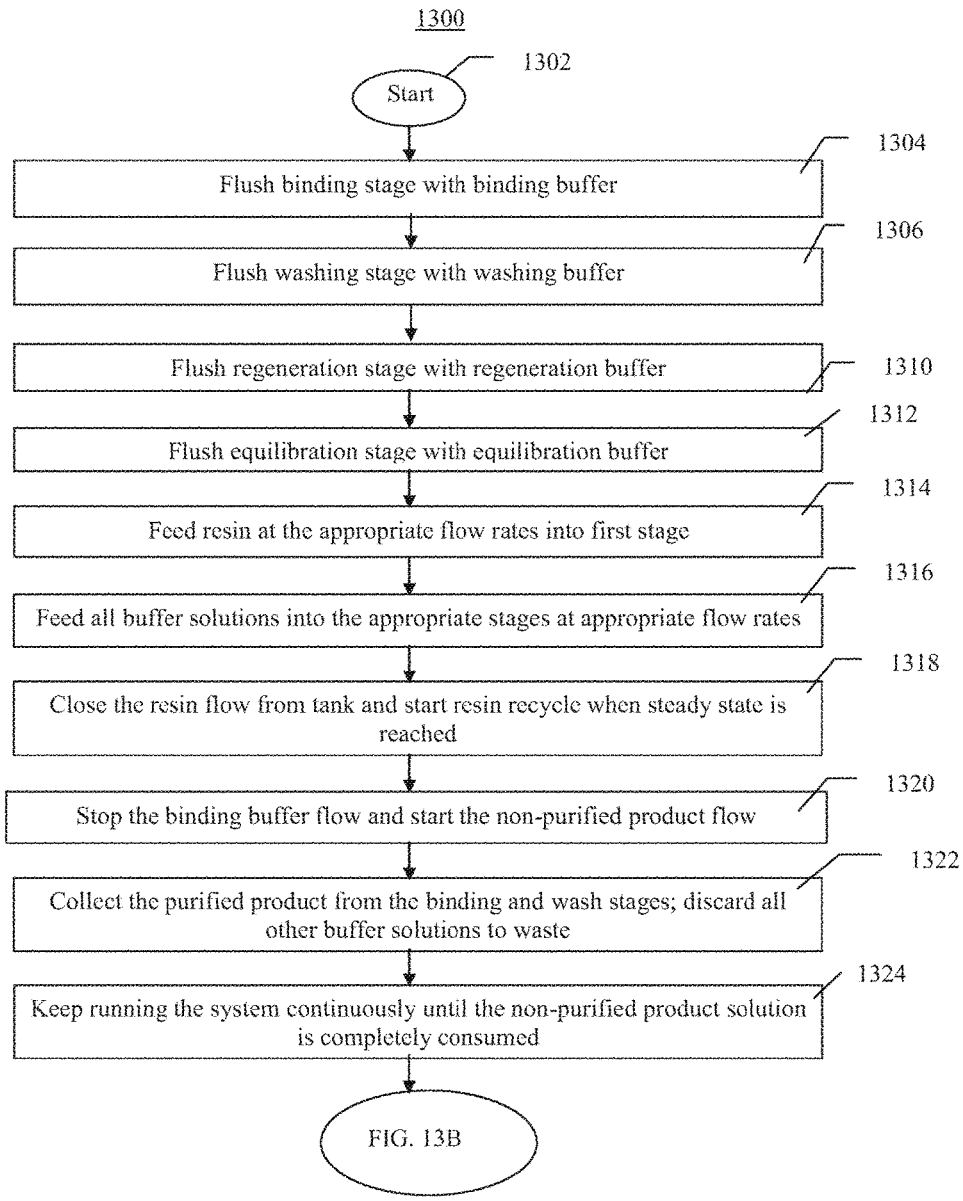
FIGS. 13A and 13B detail a process of countercurrent tangential negative chromatography operating in continuous mode, according to an embodiment of the present disclosure.
Figure 13B:
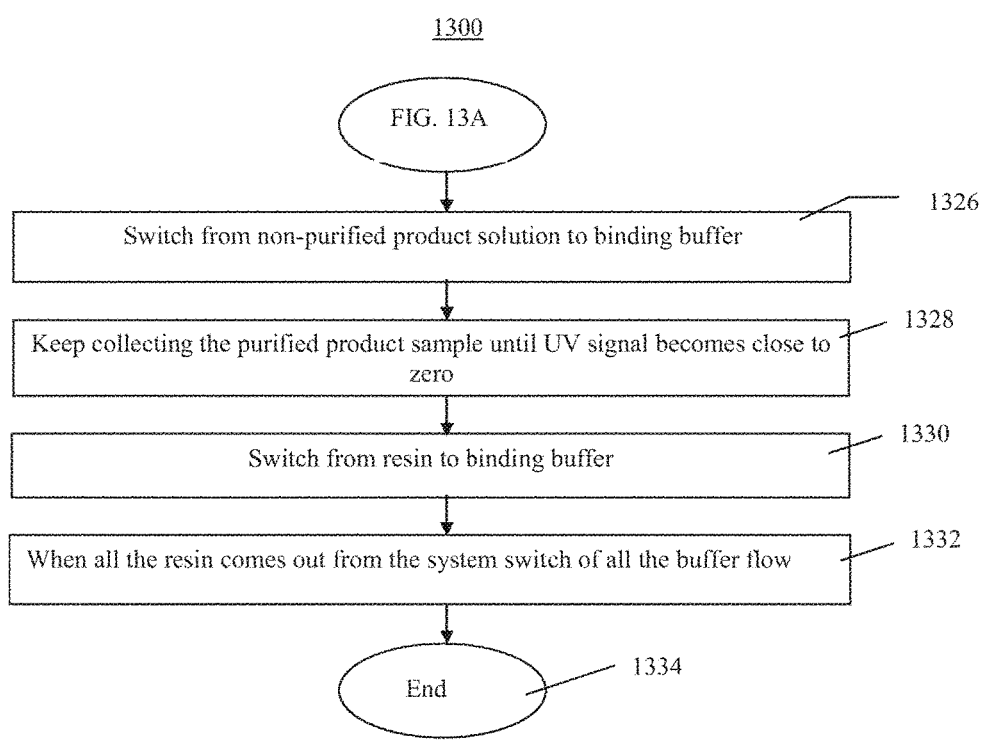

Referring to FIGS. 13A and 13B, a process 1300 of countercurrent tangential negative chromatography operating in continuous mode is shown, according to another embodiment of the present invention. Process 1300 begins in step 1302. The binding stage (Module 610 of FIG. 11) is flushed with binding buffer, as shown in step 1304. The washing stage (Module 620 of FIG. 11) is flushed with washing buffer, as shown in step 1306. The regeneration stage (Module 640 of FIG. 11) is flushed with regeneration buffer, as shown in step 1310. The equilibration stage (Module 650 of FIG. 11) is flushed with equilibration buffer, as shown in step 1312. Resin is fed at the appropriate flow rates into the first stage of the system (Module 610 of FIG. 11), as shown in step 1314. All buffer solutions are fed into the appropriate stages at appropriate flow rates, as shown in step 1316. When the resin concentration reaches steady-state, it is redirected and recycled back to the entrance of the system via the three way valve 665 and 666, as shown in step 1318. Binding buffer flow is then interchanged with the unpurified product solution, as shown in step 1320. The purified product is collected from the binding and wash stages (Modules 610 and 620 of FIG. 11), while all other buffer solutions are discarded to waste, as shown in step 1322. The entire system is kept running continuously until the non-purified product solution is completely consumed, as shown in step 1324. The non-purified product solution is then switched to binding buffer, as shown in step 1326. The purified product solution is collected in the product tank until UV280 signal is close to zero, as shown in step 1328. At the point the resin is switched off and the binding buffer is switched on as shown in step 1330. After all the resin is recovered from the system, all buffers are shut down, as shown in step 1332. The process ends and concludes in disassembly of the apparatus (1334).

Modeling

Product recovery is one of the most important cost drivers in chromatography. This is because the protein molecules in chromatography are of extremely high value. A capture chromatography process should have a recovery of at least 90%. Therefore, it was decided to model the product recovery stage of the present invention (the elution stage).

The following assumptions were made in this model:
1. The tangential flow (TFF) membranes in the module are able to process the slurry of resin and elution buffer at appropriate conversion factors (upwards of 80%).
2. The kinetics of desorption of the product molecule from the resin are fast.
3. The sieving coefficient of the TFF membrane for the product is constant throughout the process.
4. The system is "dead-space" free.

The impacts on the percent yield (% recovery) of the following variables are explored in this model:
1. "Gamma ($\gamma$)" is the ratio of elution buffer flow-rate to resin buffer flow rate, and governs the dilution of the product, buffer usage, and washing efficiency. This variable can be controlled by the operator.
2. "s" is the sieving coefficient of the TFF membrane for the product molecule. s equals the product concentration in the permeate divided by the product concentration in the fluid phase in the retentate (i.e., the concentration of unbound product in the retentate). This is an inherent property of the membrane and cannot be changed by the operator.
3. "N" is the number of stages; the present model explores a two-stage and a three-stage system in operation. As the number of stages increases, with all other variables held constant, the washing efficiency and product recovery increase. However, more stages increase the complexity and cost of the system.

Model equations were derived by using material balances and solving for % yield. It became convenient to introduce a new variable $\alpha = \gamma \cdot s$.

Equation 1 shows the percent-yield for a two-stage system as a function of $\alpha$:

$$\%\text{Yield} = \left(1 - \frac{1}{(1 + \alpha + \alpha^2)}\right) * 100\% \qquad (1)$$

Equation 2 shows the percent-yield for a three-stage system as a function of $\alpha$:

$$\%\text{Yield} = \left(1 - \frac{1}{(1 + \alpha + \alpha^2 + \alpha^3)}\right) * 100\% \qquad (2)$$

Figure 14:
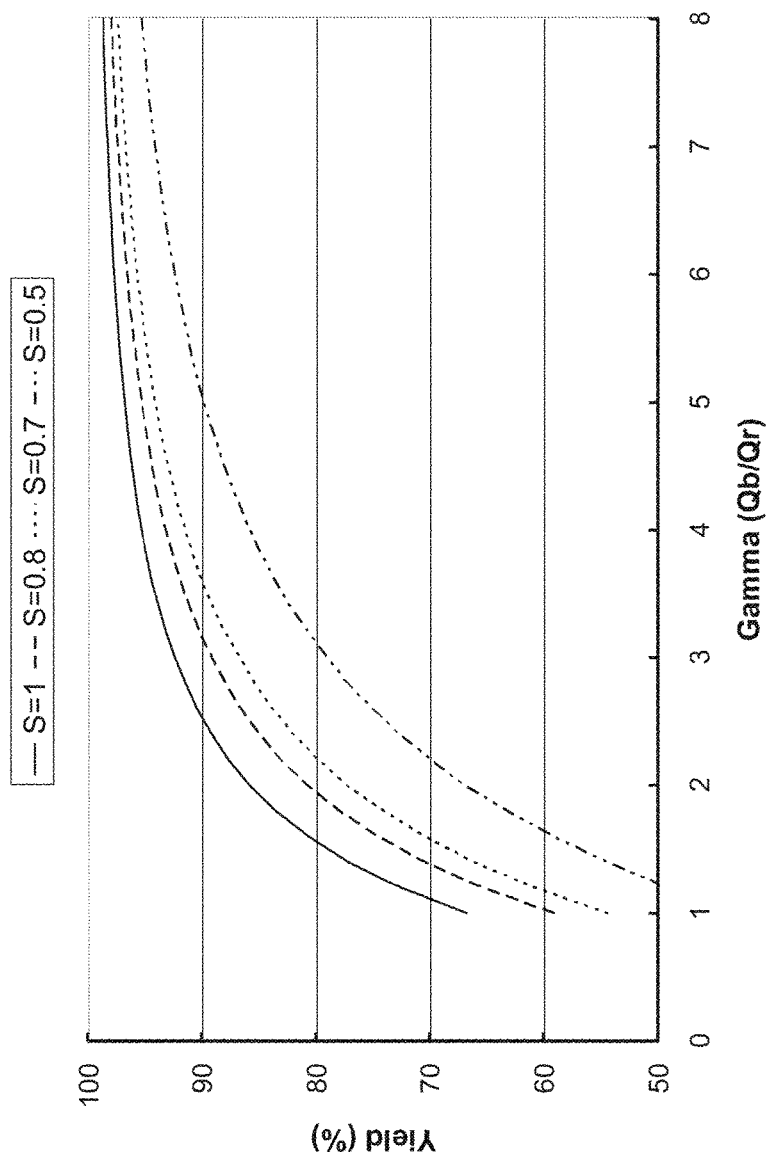
FIG. 14 discloses the results of a mathematical model of a two-stage countercurrent tangential chromatography, according to an embodiment of the present disclosure, showing a ratio of buffer to resin flow-rates (gamma) vs. percent yield for various sieving coefficients.
Figure 15:
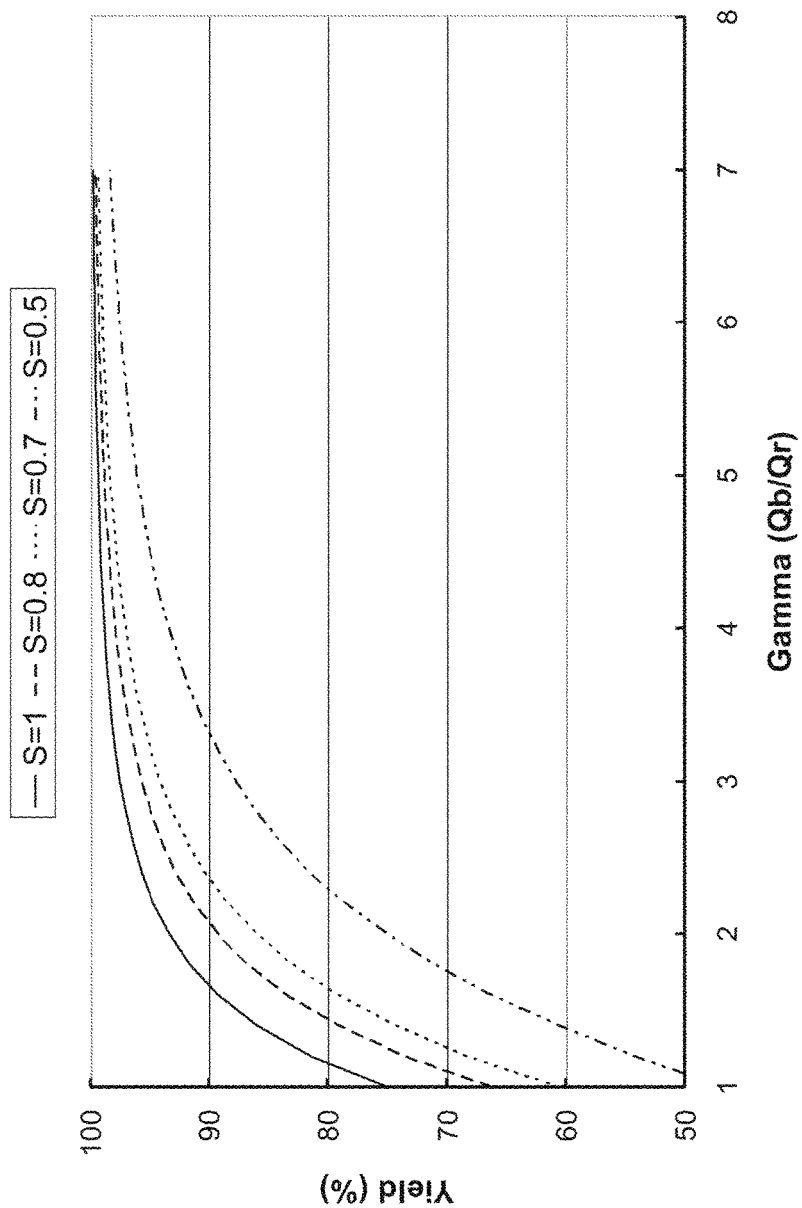
FIG. 15 discloses the results of a mathematical model of a three-stage countercurrent tangential chromatography system, according to an embodiment of the present disclosure, showing a ratio of buffer to resin flow-rates (gamma) vs. percent yield for various sieving coefficients.

FIGS. 14 and 15 show the results of this model; gamma ($\gamma$) is the independent variable, and percent (%) yield is the dependent variable. Percent yield curves are generated for specific sieving coefficients for both models (s=0.5, 0.7, 0.8, 1.0).

FIG. 14 shows the results for a two-stage countercurrent tangential chromatography system showing the percent yield as a function of the ratio of buffer to resin flow-rates (gamma) for sieving coefficients s=0.5, 0.7, 0.8, 1.0.

FIG. 15 shows the results for a three-stage countercurrent tangential chromatography system showing the percent yield as a function of the ratio of buffer to resin flow-rates (gamma) for sieving coefficients s=0.5, 0.7, 0.8, 1.0.

The results of the model show that greater than 95% yield can be achieved by both the two-stage and the three-stage systems. Sieving coefficients for these processes are expected to be within a range of [0.8-1.0] because the membranes used in this system would be microporous and would therefore be expected to pass the product molecule relatively freely. The two-stage system would need a higher buffer to feed ratio ($\gamma$) than the three-stage system to achieve the same percent (%) yield. Therefore, the recommended operating gamma ($\gamma$) for a two-stage system is 4 to 6, and for a three-stage system the recommended operating gamma ($\gamma$) is 3 to 4.

A modeling example is described herein of protein A capture of 20,000 L bioreactor harvest, 5 g/L IgG concentration, in a three-stage countercurrent tangential chromatography system operating in batch mode, as shown in FIG. 5. This example is illustrative of one of many modes of operation of the present invention.

This modeling example makes the following assumptions:
1. Residence time=0.5 min (hypothetical "small" protein A bead)
2. Resin capacity=30 g/L
3. General Electric® hollow fibers are used as the TFF membrane. The areas and hold up volumes are used from existing large scale General Electric® modules.
4. Flux=100 LMH
5. An 80% conversion factor is assumed in the TFF filters.

TABLE 1

Modeling results

| | | | |
|---|---|---|---|
| Volume | 20000 L | Binding stage time | 0.175 hrs |
| Product conc. | 5 g/L | Wash Volume 4 Resin Volumes (RV) | 1200 L |
| Total product | 100 kg | Washin stage Time | 0.120 hrs |
| Total Membrane area | 300 m2 | Elution Volume 4 Resin Volumes (RV) | 1200 L |
| # of stages | 3 | Elution stage Time | 0.12 hrs |
| Washing dilution factor | 4 | Regeneration Buffer volume (4 RV) optional | 1200 L |
| Resin Volume | 300 L | Wash Time | 0.120 hrs |
| Resin Capacity | 30 g/L | Equilibration Buffer volume (4 RV) | 1200 |
| Flux | 100 LMH | Wash Time | 0.120 hrs |
| One cycle processes | 9 kg MAB | Total Cycle time | 0.66 hrs |
| One cycle Volume | 1800 L | # of cycles | 12 |
| Residence time | 0.5 min | Total Processing Time | 7.9 hrs |
| Static mixer volume | 100 L | | |
| Total Flow | 200 L/min | | |
| Resin Flow rate | 28.6 L/min | | |
| Feed Flow rate | 171.4 L/min | | |
| Feed Flux | 34.3 LMH | | |

The results of this model show the following:

1. 20,000 L of unpurified product can be processed with 300 L of resin which represents a factor of 4 decrease from conventional column chromatography.

2. The operation can be performed in a single 8-hr shift.

3. Number of cycles can be decreased by increasing resin volume.

4. Efficiency and process time could be increased by increasing flux.

The inventor recognizes numerous and substantial advantages of the present invention to the downstream purification process, including:

1. Current technology could be readily adapted to this process because existing components are readily available in the market. Namely, the tangential flow filters (cassettes, hollow fibers and ceramic membranes) and chromatography resins are readily available. It might be advantageous to develop a new line of resins specifically designed for this invention by using smaller beads than in conventional column chromatography. This would minimize mass transfer limitations, increase dynamic binding capacity, and make the process more efficient.

2. Tangential chromatography systems according to the principles of this invention may be scaled as large as necessary, similarly to any tangential flow system. This is not the case with conventional column chromatography—the largest scalable columns in the market are currently limited to 2 meters in diameter.

3. Continuous-mode countercurrent tangential chromatography can be designed as shown in FIG. 6. In general, continuous processes are more efficient and require a smaller system size.

4. There is potential to run this system in a completely disposable manner. This is because much smaller amounts of resin are needed for this operation than in column chromatography (this would be true for cheaper resin kinds such as ion exchange resins). Additionally, the tangential flow filters at smaller scales could be used on a disposable basis as well.

5. The use of resin could be an order of magnitude lower than in conventional chromatography, causing significant cost savings by as much as 80%.

Therefore, the present inventor recognizes numerous applications of the present invention to the $850+ million/year process chromatography market.

U.S. Pat. No. 4,780,210 to Jen-Chang Hsia entitled "Tangential flow affinity ultra-filtration" describes a process for trypsin purification. More particularly, it relates to a process of biochemical purification which combines the processing techniques of affinity chromatography and tangential ultra-filtration, and is capable of being operated on a continuous flow or semi-continuous-flow basis, for use in the purification (or separation) of molecules of biological interest. The process of the present invention is verifiably different because of the countercurrent and single-pass nature, along with various other improvements. The process described in U.S. Pat. No. 4,780,210 is not suitable for the biotech market.

Accordingly, while the methods disclosed herein have been described and shown with reference to particular operations performed in a particular order, it will be understood that these operations may be combined, sub-divided, or re-ordered to form equivalent methods without departing from the teachings of the present invention. Accordingly, unless specifically indicated herein, the order and grouping of the operations is not a limitation of the present invention.

Finally, while the invention has been particularly shown and described with reference to particular embodiments thereof, it will be understood by those skilled in the art that various other changes in the form and details may be made without departing from the spirit and scope of the invention, as defined in the appended claims.

What is claimed is:

1. A module, comprising:
   a first input port for receiving an input solution;
   a first mixer for mixing the input solution with a recycled solution from a second input port to produce a first mixed output;
   a stage I filter for concentrating the first mixed output to produce stage I retentate, wherein stage I permeate exits the module from the stage I filter via a first output port;
   a second mixer for mixing the stage I retentate from the stage I filter and an optional buffer solution from a third input port to produce a second mixed output;
   a stage II filter in series with the stage I filter for concentrating the second mixed output to produce stage II retentate which exits the module from the stage II filter via a second output port, wherein stage II permeate exits the module from the stage II filter via a third output port; and
   at least one retentate pump,
   wherein:
      the input solution from input port flows through the stage I filter and the stage II filter in a single pass, and recycled solution from the third output port flows countercurrent to the input solution into the second input port;
      the stage I permeate and the stage II permeate are free from pressurization by a permeate pump; and
      the at least one retentate pump is arranged and disposed to drive and stabilize hydrodynamics of the module.

2. The module of claim 1, wherein each of the first mixer and the second mixer is preceded by a separate retentate pump.

3. The module of claim 1, wherein the input solution comprises resin slurry and unpurified product solution.

4. The module of claim 1, wherein the stage I permeate is waste.

5. The module of claim 1, wherein the stage I permeate is product.

6. The module of claim 1, wherein the second mixer receives clean buffer solution.

7. The module of claim 1, wherein the second mixer does not receive clean buffer solution.

8. The module of claim 1, wherein the third output port is connected via a pump and a three-way valve to the second input port.

9. The module of claim 8, wherein the three-way valve sends an output from the third output port either to waste, or to the second input port.

10. The module of claim 1, wherein the stage I filter and the stage II filter are tangential flow filters.

11. The module of claim 1, wherein the first mixer and the second mixer are static mixers.

12. The module of claim 1, wherein the retentate pump is disposed between the stage I filter and the second mixer.

13. The module of claim 1, wherein, the at least one retentate pump is arranged and disposed to drive and stabilize hydrodynamics of the module at steady state.

* * * * *